(12) United States Patent
Benson et al.

(10) Patent No.: US 7,217,556 B1
(45) Date of Patent: May 15, 2007

(54) CRYSTALLIZATION AND STRUCTURE DETERMINATION OF GLYCOSYLATED HUMAN BETA SECRETASE, AN ENZYME IMPLICATED IN ALZHEIMER'S DISEASE

(75) Inventors: Timothy E. Benson, Kalamazoo, MI (US); Jim D. Durbin, Portage, MI (US); Donald Bryan Prince, Parchment, MI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/028,224

(22) Filed: Dec. 21, 2001

Related U.S. Application Data

(63) Continuation of application No. 09/808,310, filed on Mar. 14, 2001, now abandoned, which is a continuation-in-part of application No. 09/747,421, filed on Dec. 23, 2000, now abandoned.

(51) Int. Cl.
*C12N 9/64* (2006.01)
*G01N 33/483* (2006.01)

(52) U.S. Cl. .............................. 435/226; 702/27; 436/2

(58) Field of Classification Search .................. 702/27; 435/226
See application file for complete search history.

(56) References Cited

U.S. PATENT DOCUMENTS

| | | | |
|---|---|---|---|
| 5,744,346 A | 4/1998 | Chrysler et al. | |
| 5,942,400 A | 8/1999 | Anderson et al. | |
| 6,221,645 B1 | 4/2001 | Chrysler et al. | |
| 6,225,103 B1 | 5/2001 | Keolsch et al. | |
| 6,245,884 B1 | 6/2001 | Hook | |
| 6,258,386 B1 | 7/2001 | Xia et al. | |
| 6,268,158 B1 | 7/2001 | Pantoliano et al. | |
| 6,291,223 B1 | 9/2001 | Christie et al. | |
| 6,297,021 B1 | 10/2001 | Nienaber et al. | |
| 6,329,163 B1 | 12/2001 | Anderson et al. | |
| 6,420,534 B1 | 7/2002 | Gurney et al. | |
| 6,440,698 B1 | 8/2002 | Gurney et al. | |
| 6,545,127 B1 * | 4/2003 | Tang et al. | 530/350 |
| 2001/0016324 A1 | 8/2001 | Gurney et al. | |
| 2001/0018208 A1 | 8/2001 | Gurney et al. | |
| 2001/0021391 A1 | 9/2001 | Gurney et al. | |
| 2002/0037315 A1 | 3/2002 | Gurney et al. | |
| 2002/0049303 A1 | 4/2002 | Tang et al. | |
| 2002/0055459 A1 * | 5/2002 | Chopra et al. | 514/1 |
| 2002/0064819 A1 | 5/2002 | Gurney et al. | |
| 2002/0081634 A1 | 6/2002 | Gurney et al. | |
| 2002/0115600 A1 | 8/2002 | Koelsch et al. | |
| 2003/0095958 A1 | 5/2003 | Bhisetti et al. | |
| 2004/0014194 A1 * | 1/2004 | Beyer et al. | 435/226 |

FOREIGN PATENT DOCUMENTS

| | | |
|---|---|---|
| WO | WO 01/17369 A2 | 3/2000 |
| WO | WO 01/00663 A2 | 1/2001 |
| WO | WO 01/00665 A2 | 1/2001 |
| WO | WO 01/23533 A2 | 4/2001 |
| WO | WO 01/49097 A2 | 7/2001 |
| WO | WO 01/49098 A2 | 7/2001 |
| WO | WO 01/50829 A2 | 7/2001 |
| WO | WO 02/25276 A1 | 3/2002 |
| WO | WO 02/053594 A2 | 7/2002 |
| WO | WO 03/012089 A3 | 2/2003 |

OTHER PUBLICATIONS

Bruinzeel et al. (2002) Prot Exp Pur 26:139-148.*
Ghosh et al. (2001) J Med Chem 44:2865-2868.*
Branden et al. "Introduction to Protein Structure Second Edition", Garland Publishing Inc., New York, 1999.*
Hong et al. (2000) Science 290:150-153.*
Farzan et al. (2000) Proc Natl Acad Sci, USA 97:9712-9717.*
Ehehalt et al. (2002) Biochem Biophys Res Commun 293:30-37.*
"Encyclopedia of Molecular Biology" Creighton, T., John Wiley and Sons, Inc. New York, 1999, p. 586.*
Drenth, "Principles of Protein X-ray Crystallography," Second Edition, 1994 Springer-Verlag New York, Inc., pp. 1-18.
Brünger, "X-PLOR: Version 3.1, a System for X-Ray Crystallography and NMR", Yale University Press, New Haven & London, 1992; cover page, publication page and table of contents: 13 pages.
Brünger et al., "Slow-cooling protocols for crystallographic refinement by simulated annealing," *Acta Crystallogr A.* Jul. 1, 1990;46( Pt 7):585-93.
"CNX: Crystallography and NMR eXplorer" datasheet, Accelrys Corporate Headquarters, San Diego, CA (2001). [ retrieved Aug. 30, 2002 from the Internet: <URL. http://www.accelrys.com>; 2 pgs.].
Epps et al., "The ligand affinity of proteins measured by isothermal denaturation kinetics," *Anal Biochem.* May 1, 2001;292(1):40-50.
Otwinowski, "Maximum Likelihood Refinement of Heavy Atom Parameters," *Isomorphous Replacement and Anomalous Scattering*, Wolf et al., eds., Science & Engineering Research Council, Daresbury Laboratory, Warrington, U.K., Proceedings of the CCP4 Study Weekend, Jan. 25-26, 1991; pp. 80-86.
Research Collaboratory for Structural Bioinformatics, "Protein Data Bank," [online] United States; retrieved Aug. 30, 2002 from the Internet: <URL. http://www.rcsb.org/pdb/> 8 pages.
Bartlett et al., "CAVEAT: A program to facilitate the structure-derived design of biologically active molecules," *Molecular Recognition: Chemical and Biological Problems*, Royal Society of Chemistry, Special Pub No. 78:182-196 (1989).
Benson et al., "An enzyme-substrate complex involved in bacterial cell wall biosynthesis," *Nat Struct Biol.* Aug. 1995;2(8):644-53.
Berman et al., "The Protein Data Bank," *Nucleic Acids Res.* Jan. 1, 2000;28(1):235-42.
Blundell et al., *Protein Crystallography*, Academic Press, New York, NY; title page, publication page, and table of contents only, 8 pages (1976).

(Continued)

*Primary Examiner*—David J. Steadman
(74) *Attorney, Agent, or Firm*—Steve Zelson; E. Victor Donahue

(57) ABSTRACT

The x-ray crystal structure of BACE or BACE-like proteins is useful for solving the structure of other molecules or molecular complexes, and identifying and/or designing potential modifiers of BACE activity.

1 Claim, 6 Drawing Sheets

OTHER PUBLICATIONS

Böhm, "The computer program LUDI: a new method for the de novo design of enzyme inhibitors," *J Comput Aided Mol Des*. Feb. 1992;6(1):61-78.

Collaborative Computational Project, No. 4, "The CCP4 suite: programs for protein crystallography" *Acta Cryst*. 1994;D50:760-3.

Eisen et al., "HOOK: a program for finding novel molecular architectures that satisfy the chemical and steric requirements of a macromolecule binding site," *Proteins: Struct. Funct. Genet*. Jul. 1994;19(3):199-221.

Ermolieff et al., "Proteolytic activation of recombinant pro-memapsin 2 (pro-beta-secretase) studied with new fluorogenic substrates," *Biochemistry*. Oct. 10, 2000;39(40):12450-6.

Fairlie et al., "Conformational selection of inhibitors and substrates by proteolytic enzymes: implications for drug design and polypeptide processing," *J Med Chem*. Apr. 6, 2000;43(7):1271-81.

Finzel, "LORE: exploiting database of known structures," *Meth. Enzymol*. 1997; 277(B):230-42.

Gillet et al., "SPROUT: a program for structure generation," *J Comput Aided Mol Des*. Apr. 1993;7(2):127-53.

Goodford, "A computational procedure for determining energetically favorable binding sites on biologically important macromolecules," *J Med Chem*. Jul. 1985; 28(7):849-57.

Goodsell et al., "Automated docking of substrates to proteins by simulated annealing," *Proteins: Struct. Funct. Genet*. 1990;8(3):195-202.

Haniu et al., "Characterization of Alzheimer's beta -secretase protein BACE. A pepsin family member with unusual properties," *J Biol Chem*. Jul. 14, 2000;275(28):21099-106.

Hendrickson et al., "Selenomethionyl proteins produced for analysis by multi-wavelength anomalous diffraction (MAD): a vehicle for direct determination of three-dimensional structure," *EMBO J*. May 1990;9(5):1665-72.

Hong et al., "Structure of the protease domain of memapsin 2 (β-secretase) complexed with inhibitor," *Science*. Oct. 6, 2000;290(5489):150-3.

Huang et al., "A 3D-stuctural model of memapsin 2 protease generated from theoretical study," *Acta Pharmacol Sin*. Jan. 2001;22(1):50-56.

Hussain et al., "Identification of a novel aspartic protease (Asp 2) as β-secretase," *Mol Cell Neurosci*. Dec. 1999;14(6):419-27.

Jiang et al., "Protein hydration observed by X-ray diffraction. Solvation properties of penicillopepsin and neuraminidase crystal structures," *J Mol Biol*. Oct. 14, 1994;243(1):100-15.

Kang et al., "The precursor of Alzheimer's disease amyloid A4 protein resembles a cell-surface receptor," *Nature*. Feb. 19, 1987;325(6106):733-6.

Kitaguchi et al., "Novel precursor of Alzheimer's disease amyloid protein shows protease inhibitory activity," *Nature*. Feb. 11, 1988;331(6156):530-2.

Kuntz et al., "A geometric approach to macromolecule-ligand interactions," *J Mol Biol*. Oct. 25, 1982;161(2):269-88.

Lattman, "Use of the rotation and translation functions," *Methods Enzymol*. 1985;115:55-77.

Lauri et al., "CAVEAT: a program to facilitate the design of organic molecules," *J Comput Aided Mol Des*. Feb. 1994;8(1):51-66.

Lin et al., "Human aspartic protease memapsin 2 cleaves the β-secretase site of β-amyloid precursor protein," *Proc Natl Acad Sci U S A*. Feb. 15, 2000;97(4):1456-60.

Mallender et al., "Characterization of recombinant, soluble beta-secretase from an insect cell expression system," *Mol Pharmacol*. Mar. 2001;59(3):619-26.

Martin, "3D database searching in drug design," *J Med Chem*. Jun. 12, 1992; 35(12):2145-54.

Meng et al., "Automated docking with grid-based energy evaluation," *J. Comp. Chem*, May 1992;13(4):505-524.

Miranker et al., "Functionality maps of binding sites: a multiple copy simultaneous search method," *Proteins: Struct. Funct. Genet*. 1991;11(1):29-34.

National Institutes of Health, "BLAST 2 Sequences," [online] United States; retrieved Aug. 29, 2001 from the Internet: <URL:http://www.ncbi.nlm.nih.gov/gorf/b12.html>, 1 pg.

Navaza, "AMoRe: an automated package for molecular replacement," *Acta Cryst*. 1994;A50:157-163.

Nishibata et al., "Automatic creation of drug candidate structures based on receptor structure. Starting point for artificial lead generation," *Tetrahedron*, 1991;47(43):8985-90.

Noren et al., "A general method for site-specific incorporation of unnatural amino acids into proteins," *Science*. Apr. 14, 1989;244(4901):182-8.

Park et al., "Molecular Characterization of Candidate β-secretases, BACE1 and BACE2," ScholarOne, Inc. [online] Session No. 180.11; Society for Neuroscience's 30th Annual Meeting, New Orleans, LA, Nov. 4-9, 20001 [retrieved on Oct. 29, 2001]. Retrieved from the Internet URL: <http://sfn.scholarone.com/itin2000/main.html?new_page_id=76&abstract_id=19280&is_tech=0>, 1 page.

Ponte et al., "A new A4 amyloid mRNA contains a domain homologous to serin proteinase inhibitors," *Nature*. Feb. 11, 1988;331(6156):525-7.

Research Collaboratory for Structural Bioinformatics, "Protein Data Bank," [online] United States; retrieved Apr. 9, 2001 from the Internet: <URL:http://www.rcsb.org/pdb/> 2 pages.

Rossman, ed., *The Molecular Replacement Method—A Collection of Papers on the Use of Non-Crystallographic Symmetry, Intl. Sci. Rev. Ser. No. 13*, Gordon & Breach, New York, NY; title page, publication page, and table of contents only, 6 pages (1972).

Sack, "CHAIN—A Crystallographic Modeling Program," *J Molecular Graphics*. Dec. 1988; 6(4):224-5.

Sauder et al., "Modeling of substrate specificity of the Alzheimer's disease amyloid precursor protein beta-secretase," *J Mol Biol*. Jul. 7, 2000;300(2):241-8.

Shi et al., "The pro domain of β-secretase does not confer strict zymogen-like properties but does assist proper folding of the protease domain," *J Biol Chem*. Mar. 30, 2001;276(13):10366-73.

Sinha et al. "Purification and cloning of amyloid precursor protein β-secretase from human brain," *Nature*. Dec. 2, 1999;402(6761):537-40.

Skovronsky et al., "Beta-secretase revealed: starting gate for race to novel therapies for Alzheimer's disease," *Trends Pharmacol Sci*. May 2000;21(5):161-3.

Tanzi et al. "Protease inhibitor domain encoded by an amyloid protein precursor mRNA associated with Alzheimer's disease," *Nature*. Feb. 11, 1988;331(6156):528-30.

Tatusova et al., "BLAST 2 Sequences, a new tool for comparing protein and nucleotide sequences," *FEMS Microbiol Lett*. May 15, 1999;174(2)247-50.

Travis, "Proteins and organic solvents make an eye-opening mix," *Science*. Nov. 26, 1993;262(5138):1374.

Turner et al., "Substrate specificity of memapsin 2 (beta-secretase): Basis for inhibitor drug design for Alzheimer's disease," Experimental Biology 2001 Conference. Orlando, Florida, USA. Mar. 31-Apr. 4, 2001. Abstracts, part I. *FASEB J*. Mar. 7, 2001;15(4):A538.

Van Duyne et al., "Atomic Structures of the human immunophilin FKBP-12 complexes with FK506 and rapamycin," *J Mol Biol*. Jan. 5, 1993;229(1):105-24.

Vassar et al. "B-secretase cleavage of Alzheimer's amyloid precursor protein by the transmembrane aspartic protease BACE," *Science*. Oct. 22, 1999;286(5440):735-41.

Wyckoff et al., eds., *Methods in Enzymology vol. 114—Diffraction Methods for Biological Macromolecules*, Academic Press, Orlando, FL; title page, publication page, and table of contents only, 5 pages (1985).

Wyckoff et al., eds., *Methods in Enzymology vol. 115. Diffraction Methods for Biological Macromolecules*, Academic Press, Orlando, FL; title page, publication page, and table of contents only, 4 pages (1985).

Yan et al. (1999), "Membrane-anchored aspartyl protease with Alzheimer's disease β-secretase activity," *Nature*. Dec. 2, 1999;402(6761):533-7.

Alvares et al., "Rat urate oxidase produced by recombinant baculovirus expression: Formation of peroxisome crystalloid core-like structures," *Proc. Natl Acad. Sci. USA*, Jun. 1992;89:4908-4912.

Dealwis et al., "X-ray Analysis at 2.0 Å Resolution of Mouse Submaxillary Renin Complexed with a Decapeptide Inhibitor CH-66, Based on the 4-16 Fragment of Rat Angiotensinogen," *J Mol Biol*, 1994;236:342-360.

Giegé et al., "Crystallogenesis of Biological Macromolecules: Facts and Perspectives," *Acta Cryst.*, 1994;D50:339-350.

Kervinen et al., "Toward a universal inhibitor of retroviral proteases: Comparative analysis of the interactions of LP-130 complexed with proteases from HIV-1, FIV, and E1AV," *Protein Science*, Nov. 1998;7:2314-2323.

McPherson et al., "The Science of Macromolecular crystallization," *Structure*, Aug. 15, 1995;3:759-768.

Tang et al., "Structural evidence for gene duplication in the evolution of the acid proteases," *Nature*, Feb. 16, 1978;271:618-621.

Van Der Klei et al., "Biosynthesis and Assembly of Alcohol Oxidase, A Peroxisomal Matrix Protein in Methylotrophic Yeasts: A Review," *Yeast*, 1991;7:195-209.

Wang et al., "Crystallization of glycosylated human BACE protease domain expressed in Trichoplusia ni," *Biochimica et Biophysica Acta*, 2004;1698:255-259. (Available online Jan. 21, 2004).

Witkowski et al., "Conversion of a β-Ketoacyl Synthase to a Malonyl Decarboxylase by Replacement of the Active-Site Cysteine with Glutamine," *Biochemistry*, 1998;38:11643-11650. (Published on Web Aug. 18, 1999).

\* cited by examiner

Fig. 7

SEQ ID NO:1

EMVDNLRGKSGQGYYVEMTVGSPPQTLNILVDTGSSNFAVGAAPHPFLHRYYQR
QLSSTYRDLRKGVYVPYTQGKWEGELGTDLVSIPHGPNVTVRANIAAITESDKFFINGSN
WEGILGLAYAEIARPDDSLEPFFDSLVKQTHVPNLFSLQLCGAGFPLNQSEVLASVGGSM
IIGGIDHSLYTGSLWYTPIRREWYYEVIIVRVEINGQDLKMDCKEYNYDKSIVDSGTTNL
RLPKKVFEAAVKSIKAASSTEKFPDGFWLGEQLVCWQAGTTPWNIFPVISLYLMGEVTNQ
SFRITILPQQYLRPVEDVATSQDDCYKFAISQSSTGTVMGAVIMEGFYVVFDRARKRIGF
AVSACHVHDEFRTAAVEGPFVTLDMEDCGYN

CRYSTALLIZATION AND STRUCTURE DETERMINATION OF GLYCOSYLATED HUMAN BETA SECRETASE, AN ENZYME IMPLICATED IN ALZHEIMER'S DISEASE

RELATED APPLICATIONS

This is a continuation of U.S. application Ser. No. 09/808,310, filed Mar. 14, 2001 now abandoned, which is a continuation-in-part of U.S. application Ser. No. 09/747,421, filed Dec. 23, 2000 now abandoned, both of which are incorporated herein by reference in their entireties.

This application incorporates by reference the material contained on the duplicate (2) compact discs submitted herewith. Each disc contains the following files:

| Name | Size | Contents | Date of File Creation |
|---|---|---|---|
| table__1.txt | 241 KB | Table 1 | Feb. 15, 2001 |
| table__2.txt | 849 KB | Table 2 | Feb. 15, 2001 |
| table__3.txt | 235 KB | Table 3 | Feb. 15, 2001 |
| table__4.txt | 774 KB | Table 4 | Feb. 15, 2001 |

FIELD OF THE INVENTION

This invention relates to the crystallization and structure determination of beta secretase, also known as memapsin 2 and BACE, from human (*Homo sapiens*), particularly in a glycosylated form as expressed in Chinese hamster ovary (CHO), HEK293 cells, or in insect cells as part of a Baculovirus expression system.

BACKGROUND

Alzheimer's disease (AD) causes progressive dementia with consequent formation of amyloid plaques, neurofibrillary tangles, gliosis and neuronal loss. The disease occurs in both genetic and sporadic forms whose clinical course and pathological features are quite similar. Three genes have been discovered to date which, when mutated, cause an autosomal dominant form of Alzheimer's disease. These encode the amyloid protein precursor (APP) and two related proteins, presenilin-1 (PS1) and presenilin-2 (PS2), which, as their names suggest, are structurally and functionally related. Mutations in any of the three proteins have been observed to enhance proteolytic processing of APP via an intracellular pathway that produces amyloid beta peptide (Aβ peptide, or sometimes here as Abeta), a 40–42 amino acid long peptide that is the primary component of amyloid plaque in AD.

Dysregulation of intracellular pathways for proteolytic processing may be central to the pathophysiology of AD. In the case of plaque formation, mutations in APP, PS1 or PS2 consistently alter the proteolytic processing of APP so as to enhance formation of Aβ 1–42, a form of the Aβ peptide which seems to be particularly amyloidogenic, and thus very important in AD. Different forms of APP range in size from 695–770 amino acids, localize to the cell surface, and have a single C-terminal transmembrane domain. The Abeta peptide is derived from a region of APP adjacent to and containing a portion of the transmembrane domain. Normally, processing of APP at the α-secretase site cleaves the midregion of the Aβ sequence adjacent to the membrane and releases the soluble, extracellular domain of APP from the cell surface. This α-secretase APP processing creates soluble APP-α, which is normal and not thought to contribute to AD. Pathological processing of APP at the β- and γ-secretase sites, which are located N-terminal and C-terminal to the α-secretase site, respectively, produces a very different result than processing at the α site. Sequential processing at the β- and γ-secretase sites releases the Aβ peptide, a peptide possibly very important in AD pathogenesis. Processing at the β- and γ-secretase sites can occur in both the endoplasmic reticulum (in neurons) and in the endosomal/lysosomal pathway after reinternalization of cell surface APP (in all cells). Despite intense efforts, for 10 years or more, to identify the enzymes responsible for processing APP at the β and γ sites, to produce the Aβ peptide, those proteases remained unknown until recently.

The identification and characterization of the β secretase enzyme, termed Aspartyl Protease 2 (Asp2) has been established. In addition, the X-ray crystal structure of human beta secretase in complex with a peptide inhibitor was solved and published Hong et al., *Science* 290: 150–53 (2000) from protein expressed in *E. coli* that contained no covalent sugar (glycosylation) at any of the four putative glycosylation sites within the enzyme.

SUMMARY OF THE INVENTION

This invention relates to the crystallization and structure determination of beta secretase, also known as memapsin 2 and BACE, from human (*Homo sapiens*), particularly in a glycosylated form as expressed in Chinese hamster ovary (CHO), HEK293 cells, or in insect cells as part of a Baculovirus expression system.

In one aspect, the present invention provides a method for crystallizing a human beta secretase molecule or molecular complex. The method involves crystallizing a human beta secretase molecule or molecular complex by preparing purified human beta secretase in the presence of an inhibitor and crystallizing human beta secretase from a solution having a pH of about 3.5 to about 5.5.

In another aspect, the present invention provides crystalline forms of a human beta secretase molecule. In one embodiment, a crystal of human beta secretase is provided having the trigonal space group symmetry P3$_2$21 with unit cell dimensions of a, b, and c, wherein a is about 77 Å to about 147 Å, b is about 77 Å to about 147 Å, and c is about 75 Å to about 145 Å; and a=β=90', and γ=120°. Preferably, the crystal has unit cell dimensions of a=112.0 Å, b=112 Å, c=110 Å, α=β=90°, γ=120°.

In another aspect, the present invention provides a glycosylated molecule or molecular complex that includes at least a portion of a human beta secretase binding pocket, wherein the binding pocket includes the amino acids listed in Table 5, the binding pocket being defined by a set of points having a root mean square deviation of less than about 0.43 Å from points representing the backbone atoms of said amino acids as represented by the structure coordinates listed in Table 1 or Table 3.

In another aspect, the present invention provides a molecule or molecular complex that is structurally homologous to a human beta secretase molecule or molecular complex that forms a crystal having unit cell dimensions a=112.0±35 Å, b=112±35 Å, c=110±35 Å, α=β90°, and γ=120°, wherein the human beta secretase molecule or molecular complex is represented by at least a portion of the structure coordinates listed in Table 1 or Table 3.

In another aspect, the present invention provides a scalable three-dimensional configuration of points, at least a portion of said points derived from structure coordinates of at least a portion of a human beta secretase molecule or molecular complex listed in Table 1 or Table 3 including at least one of a human beta secretase or beta secretase-like binding pocket, wherein the human beta secretase molecule or molecular complex forms a crystal having the trigonal space group symmetry $P3_221$.

In another aspect, the present invention provides a scalable three-dimensional configuration of points, at least a portion of said points derived from structure coordinates of at least a portion of a human beta secretase molecular complex listed in Table 1 or Table 3 including at least one of a human beta secretase or beta secretase-like binding pocket.

In another aspect, the present invention provides a scalable three-dimensional configuration of points, at least a portion of the points derived from structure coordinates of at least a portion of a molecule or a molecular complex that is structurally homologous to a human beta secretase molecule or molecular complex and includes at least one of a human beta secretase or beta secretase-like binding pocket, wherein the human beta secretase molecule or molecular complex forms a crystal having the trigonal space group symmetry $P3_221$.

In another aspect, the present invention provides a machine-readable data storage medium including a data storage material encoded with machine readable data which, when using a machine programmed with instructions for using said data, is capable of displaying a graphical three-dimensional representation of at least one glycosylated molecule or molecular complex selected from the group consisting of:

(i) a glycosylated molecule or molecular complex including at least a portion of a human beta secretase or beta secretase-like binding pocket including the amino acids listed in Table 5, the binding pocket defined by a set of points having a root mean square deviation of less than about 0.43 Å from points representing the backbone atoms of said amino acids as represented by structure coordinates listed in Table 1 or Table 3; (ii) a glycosylated molecule or molecular complex including at least a portion of a human beta secretase or beta secretase-like binding pocket including the amino acids listed in Table 6, the binding pocket defined by a set of points having a root mean square deviation of less than about 0.43 Å from points representing the backbone atoms of said amino acids as represented by structure coordinates listed in Table 1 or Table 3; and (iii) a glycosylated molecule or molecular complex that is structurally homologous to an human beta secretase molecule or molecular complex, wherein the human beta secretase molecule or molecular complex is represented by at least a portion of the structure coordinates listed in Table 1 or Table 3.

In another aspect, the present invention provides a machine-readable data storage medium including a data storage material encoded with a first set of machine readable data which, when combined with a second set of machine readable data, using a machine programmed with instructions for using said first set of data and said second set of data, can determine at least a portion of the structure coordinates corresponding to the second set of machine readable data, wherein said first set of data includes a Fourier transform of at least a portion of the structural coordinates for human beta secretase listed in Table 1 or Table 3, wherein the human beta secretase molecule or molecular complex forms a crystal having unit cell dimensions a=112.0±35 Å, b=112±35 Å, c=110+35 Å, $\alpha=\beta=90°$, $\gamma=120°$; and said second set of data includes an x-ray diffraction pattern of a molecule or molecular complex of unknown structure.

In another aspect, the present invention provides a method for obtaining structural information about a molecule or a molecular complex of unknown structure including: crystallizing the molecule or molecular complex; generating an x-ray diffraction pattern from the crystallized molecule or molecular complex; and applying at least a portion of the structure coordinates for human beta secretase set forth in Table 1 or Table 3 to the x-ray diffraction pattern to generate a three-dimensional electron density map of at least a portion of the molecule or molecular complex whose structure is unknown.

In another aspect, the present invention provides a method for homology modeling an human beta secretase homolog including: aligning the amino acid sequence of an human beta secretase homolog with an amino acid sequence of human beta secretase and incorporating the sequence of the human beta secretase homolog into a model of human beta secretase derived from human beta secretase structure coordinates set forth in Table 1 or Table 3 to yield a preliminary model of the human beta secretase homolog, wherein the human beta secretase forms a crystal having unit cell dimensions a=112.0±35 Å, b=112±35 Å, c=110±35 Å, $\alpha=\beta=90°$, and $\gamma 120°$; subjecting the preliminary model to energy minimization to yield an energy minimized model; and remodeling regions of the energy minimized model where stereochemistry restraints are violated to yield a final model of the human beta secretase homolog.

In another aspect, the present invention provides a computer-assisted method for identifying an inhibitor of human beta secretase activity including: supplying a computer modeling application with a set of structure coordinates of a molecule or molecular complex that forms a crystal having the trigonal space group symmetry $P3_221$, the molecule or molecular complex including at least a portion of an human beta secretase or beta secretase-like binding pocket, the binding pocket including the amino acids listed in Table 5; supplying the computer modeling application with a set of structure coordinates of a chemical entity; and determining whether the chemical entity is an inhibitor expected to bind to or interfere with the molecule or molecular complex, wherein binding to or interfering with the molecule or molecular complex is indicative of potential inhibition of human beta secretase activity.

In another aspect, the present invention provides a computer-assisted method for designing an inhibitor of human beta secretase activity including: supplying a computer modeling application with a set of structure coordinates of a molecule or molecular complex that forms a crystal having unit cell dimensions a=112.0±35 Å, b=112±35 Å, c=110±35 Å, $\alpha==90°$, and $\gamma 120°$, the molecule or molecular complex including at least a portion of a human beta secretase or beta secretase-like binding pocket, the binding pocket including the amino acids listed in Table 5; supplying the computer modeling application with a set of structure coordinates for a chemical entity; evaluating the potential binding interactions between the chemical entity and inhibitor binding pocket of the molecule or molecular complex; structurally modifying the chemical entity to yield a set of structure coordinates for a modified chemical entity; and determining whether the modified chemical entity is an inhibitor expected to bind to or interfere with the molecule or molecular complex, wherein binding to or interfering with the molecule or molecular complex is indicative of potential inhibition of human beta secretase activity.

In another aspect, the present invention provides a method for making an inhibitor of human beta secretase activity, the method including chemically or enzymatically synthesizing a chemical entity to yield an inhibitor of human beta secretase activity, the chemical entity having been identified during a computer-assisted process including supplying a computer modeling application with a set of structure coordinates of a glycosylated molecule or molecular complex, the molecule or molecular complex including at least a portion of at least one of a human beta secretase or beta secretase-like binding pocket; supplying the computer modeling application with a set of structure coordinates of a chemical entity; and determining whether the chemical entity is expected to bind to or interfere with the molecule or molecular complex at a binding pocket, wherein binding to or interfering with the molecule or molecular complex is indicative of potential inhibition of human beta secretase activity.

In another aspect, the present invention provides a method for making an inhibitor of human beta secretase activity, the method including chemically or enzymatically synthesizing a chemical entity to yield an inhibitor of human beta secretase activity, the chemical entity having been designed during a computer-assisted process including supplying a computer modeling application with a set of structure coordinates of a molecule or molecular complex that forms a crystal having unit cell dimensions a=112.0+35 Å, b=112±35 Å, c=110±35 Å, $\alpha=\beta=$ °, and $\gamma=120°$, the molecule or molecular complex including at least a portion of at least one of a human beta secretase or beta secretase-like binding pocket; supplying the computer modeling application with a set of structure coordinates for a chemical entity; evaluating the potential binding interactions between the chemical entity and a binding pocket of the molecule or molecular complex; structurally modifying the chemical entity to yield a set of structure coordinates for a modified chemical entity; and determining whether the chemical entity is expected to bind to or interfere with the molecule or molecular complex at the binding pocket, wherein binding to or interfering with the molecule or molecular complex is indicative of potential inhibition of human beta secretase activity.

In another aspect, the present invention provides a method for making an inhibitor of human beta secretase activity, the method including chemically or enzymatically synthesizing a chemical entity to yield an inhibitor of human beta secretase activity, the chemical entity having been designed during a computer-assisted process including supplying a computer modeling application with a set of structure coordinates of a molecule or molecular complex, wherein the human beta secretase molecule or molecular complex forms a crystal having the trigonal space group symmetry $P3_221$ and the molecule or molecular complex includes at least a portion of at least one of a human beta secretase or beta secretase-like binding pocket; computationally building a chemical entity represented by set of structure coordinates; and determining whether the chemical entity is expected to bind to or interfere with the molecule or molecular complex at a binding pocket, wherein binding to or interfering with the molecule or molecular complex is indicative of potential inhibition of human beta secretase activity.

In another aspect, the present invention provides a method for crystallizing a human beta secretase molecule or molecular complex including: preparing purified human beta secretase in the presence of an inhibitor; and crystallizing human beta secretase from a solution having a pH of about 3.5 to about 5.5.

In another aspect, the present invention provides a crystal of beta secretase having the trigonal space group symmetry $P3_221$.

In another aspect, the present invention provides a crystal of beta secretase including a unit cell having dimensions of a, b, and c, wherein a is about 77 Å to about 147 Å, b is about 77 Å to about 147 Å, and c is about 77 Å to about 147 Å; and $\alpha=\beta=90°$, and $\gamma=120°$.

In another aspect, the present invention provides a crystal of beta secretase having the trigonal space group symmetry $P3_221$ and including a unit cell having dimensions of a, b, and c, wherein a is about 77 Å to about 147 Å, b is about 77 Å to about 147 Å, and c is about 77 Å to about 147 Å; and $\alpha=\beta=90'$, and $\gamma=120°$.

In another aspect, the present invention provides a method of producing human beta secretase, the method including expressing the human beta secretase in a mammalian cell line.

In another aspect, the present invention provides a method of producing human beta secretase, the method including expressing the human beta secretase in an insect cell line.

Definitions

Two crystallographic data sets (with structure factors F) are considered isomorphous if, after scaling, $$\frac{\Delta F}{F} = \frac{\Sigma |F_1 - F_2|}{\Sigma F_1}$$

is less than about 35% for the reflections between 8 Å and 4 Å.

Abbreviations

The following abbreviations are used throughout this disclosure:

Alzheimer's disease (AD)

Amyloid beta peptide (Aβ peptide or Abeta)

Amyloid protein precursor (APP)

Aspartyl protease 2 (Asp2)

Baculovirus expression system (BVES)

Beta secretase (memapsin 2, BACE)

Chinese hamster ovary (CHO)

Dimethyl sulfoxide (DMSO)

Multiple anomalous dispersion (MAD)

Presenilin-1 (PS1)

Presenilin-2 (PS2)

Polyethylene glycol (PEG)

The following amino acid abbreviations are used throughout this disclosure:

A = Ala = Alanine
V = Val = Valine
L = Leu = Leucine
I = Ile = Isoleucine
P = Pro = Proline
F = Phe = Phenylalanine
W = Trp = Tryptophan
M = Met = Methionine
G = Gly = Glycine -continued S = Ser = Serine
T = Thr = Threonine
C = Cys = Cysteine
Y = Tyr = Tyrosine
N = Asn = Asparagine
Q = Gln = Glutamine
D = Asp = Aspartic Acid
E = Glu = Glutamic Acid
K = Lys = Lysine
R = Arg = Arginine
H = His = Histidine

BRIEF DESCRIPTION OF THE FIGURES

FIG. 7 depicts the sequence (SEQ ID NO:1) of residues for recombinant human beta secretase present in the X-ray structure.

DETAILED DESCRIPTION OF THE INVENTION

Figure 1:
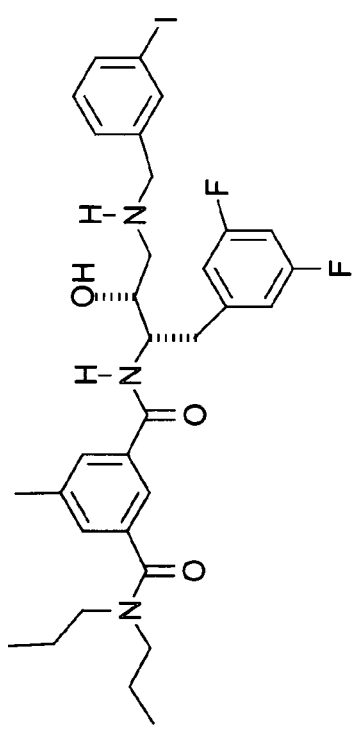
FIG. 1 is an illustration of the chemical structure of an inhibitor used in Co-crystallization experiments.

Tables 1 and 3 list atomic structure coordinates derived by x-ray diffraction of a crystal of human beta secretase expressed in CHO cells (Table 1) or Baculovirus produced human beta secretase (Table 3). Column 2 lists a number for the atom in the structure. Column 3 lists the element whose coordinates are measured. The first letter in the column defines the element. Column 4 lists the type of amino acid. Column 5 lists a number for the amino acid in the structure. Columns 6–8 list the crystallographic coordinates X, Y, and Z respectively. The crystallographic coordinates define the atomic position of the element measured. Column 9 lists an occupancy factor that refers to the fraction of the molecules in which each atom occupies the position specified by the coordinates. A value of "1" indicates that each atom has the same conformation, i.e., the same position, in all molecules of the crystal. Column 10 lists a thermal factor "B" that measures movement of the atom around its atomic center.

Tables 2 and 4 list structure factors and multiple anomalous dispersion phases for crystal structures derived by x-ray diffraction of a crystal of human beta secretase expressed in CHO cells (Table 2) or Baculovirus produced human beta secretase (Table 4). Columns 2–4 refer to the indices of the lattice planes h, k, and 1, respectively. Column 5 refers to the structure factor (F) of the observed reflections (Fobs). Column 6 refers to the standard deviation (Sigma) for the observations. Column 7 refers to the test number. The set of reflections used for calculations of the free R-factor were those where test number=1.

Crystalline Form(s) and Method of Making

The three-dimensional structure of human beta secretase was solved using x-ray crystallography to 3.2 Å resolution. Accordingly, the invention includes a human beta secretase crystal and/or a crystal with human beta secretase co-crystallized with a ligand, such as an inhibitor. Preferably, the crystal has trigonal space group symmetry $P3_221$. More preferably, the crystal includes hexagonal shaped unit cells, each unit cell having dimensions a=112.0±35 Å, b=112±35 Å, c=110+35 Å, $\alpha=\beta=90'$, $\gamma 120$. The crystallized enzyme is a monomer with a single monomer in the asymmetric unit.

According to the present invention, human beta secretase can be isolated from a variety of cell lines, for example, the mammalian cell line CHO-K1 or an insect cell line.

In a preferred embodiment, molecular complexes of purified human beta secretase at a concentration of about 1 mg/ml to about 80 mg/ml may be crystallized in the presence of an inhibitor at a concentration from about 0.1 to about 10 mM, for example, by using a streak seeding procedure from a solution including about 5% by weight to about 50% by weight PEG or PEG-MME (PEG monomethyl ether), PEG-DME (PEG dimethyl ether), or polyoxyalkylenepolyamines (e.g., materials available under the trade designation JEFFAMINE from Huntsman Corp., Salt Lake City, Utah) (preferably having a number average molecular weight between about 200 and about 20,000), preferably, a salt (more preferably about 0.001 M to about 0.5 M salt), and about 0% by weight to about 20% by weight organic solvent (such as DMSO), wherein the solution is buffered to a pH of about 3.5 to about 5.5 (preferably, a pH of about 4.0 to about 4.7). Examplary salts include sodium chloride, ammonium sulfate, magnesium sulfate, lithium sulfate, or combinations thereof. Use of a buffer having a $pK_a$ of about 3 to about 6 is preferred. A "molecular complex" means a protein in covalent or non-covalent association with a chemical entity. A buffer having a $pK_a$ of between about 3 and 6 is preferred for use in the crystallization method. A particularly preferred buffer is about 10 mM to about 200 mM sodium acetate. Variation in buffer and buffer pH as well as other additives such as PEG or PEG-MME (PEG monomethyl ether), PEG-DME (PEG dimethyl ether), or polyoxyalkylenepolyamines (e.g., materials available under the trade designation JEFFAMINE from Huntsman Corp., Salt Lake City, Utah) is apparent to those skilled in the art and may result in similar crystals.

The invention further includes an human beta secretase crystal that is isomorphous with an human beta secretase crystal characterized by a unit cell having dimensions of a, b, and c; wherein a is about 77 Å to about 147 Å, b is about 77 Å to about 147 Å, and c is about 75 Å to about 145 Å; and $\alpha=\beta=90'$, and $\gamma=120°$.

X-ray Crystallographic Analysis

Each of the constituent amino acids of human beta secretase is defined by a set of structure coordinates as set forth in Table 1. The term "structure coordinates" refers to Cartesian coordinates derived from mathematical equations related to the patterns obtained on diffraction of a monochromatic beam of x-rays by the atoms (scattering centers)

of an human beta secretase complex in crystal form. The diffraction data are used to calculate an electron density map of the repeating unit of the crystal. The electron density maps are then used to establish the positions of the individual atoms of the human beta secretase protein or protein/ligand complex.

Slight variations in structure coordinates can be generated by mathematically manipulating the human beta secretase or human beta secretase/ligand structure coordinates. For example, the structure coordinates set forth in Table 1 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the human beta secretase would not be expected to significantly alter the nature of chemical entities such as ligands that could associate with the inhibitor binding pockets. In this context, the phrase "associating with" refers to a condition of proximity between a chemical entity, or portions thereof, and an human beta secretase molecule or portions thereof. The association may be non-covalent, wherein the juxtaposition is energetically favored by hydrogen bonding, van der Waals forces, or electrostatic interactions, or it may be covalent.

Thus, for example, a ligand that bound to a inhibitor binding pocket of human beta secretase would also be expected to bind to or interfere with another inhibitor binding pocket whose structure coordinates define a shape that falls within the acceptable error.

It will be readily apparent to those of skill in the art that the numbering of amino acids in other isoforms of human beta secretase may be different than that of human beta secretase expressed in CHO or HKE 293 cells.

Active Site and Other Structural Features

Applicants' invention provides information about the shape and structure of the inhibitor binding pocket of human beta secretase in the presence of an inhibitor. The secondary structure of the human beta secretase monomer includes two domains consistent with a typical aspartic protease fold.

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations helps lead to the design of drugs having more favorable associations with their target, and thus improved biological effects. Therefore, this information is valuable in designing potential inhibitors of beta secretase-like inhibitor binding pockets, as discussed in more detail below.

The term "binding pocket," as used herein, refers to a region of a molecule or molecular complex, that, as a result of its shape, favorably associates with another chemical entity. Thus, a binding pocket may include or consist of features such as cavities, surfaces, or interfaces between domains. Chemical entities that may associate with a binding pocket include, but are not limited to, cofactors, substrates, inhibitors, agonists, and antagonists.

The amino acid constituents of an human beta secretase inhibitor binding pocket as defined herein are positioned in three dimensions in accordance with the structure coordinates listed in Table 1. In one aspect, the structure coordinates defining a inhibitor binding pocket of human beta secretase include structure coordinates of all atoms in the constituent amino acids; in another aspect, the structure coordinates of a inhibitor binding pocket include structure coordinates of just the backbone atoms of the constituent atoms.

The inhibitor binding pocket of human beta secretase preferably includes the amino acids listed in Table 5, more preferably the amino acids listed in Table 6, and most preferably the amino acids listed in Table 7, as represented by the structure coordinates listed in Table 1. Alternatively, the inhibitor binding pocket of human beta secretase may be defined by those amino acids whose backbone atoms are situated within about 4 Å, more preferably within about 7 Å, most preferably within about 10 Å, of one or more constituent atoms of a bound substrate or inhibitor. In yet another alternative, the inhibitor binding pocket may be defined by those amino acids whose backbone atoms are situated within a sphere centered on the coordinates representing the alpha carbon atom of residue Thr 231, the sphere having a radius of about 15 Å, preferably about 20 Å, and more preferably about 25 Å.

The term "beta secretase-like inhibitor binding pocket" refers to a portion of a molecule or molecular complex whose shape is sufficiently similar to at least a portion of a inhibitor binding pocket of human beta secretase as to be expected to bind related structural analogues. A structurally equivalent inhibitor binding pocket is defined by a root mean square deviation from the structure coordinates of the backbone atoms of the amino acids that make up inhibitor binding pockets in human beta secretase (as set forth in Table 1) of at most about 0.35 Å. How this calculation is obtained is described below.

Accordingly, the invention provides molecules or molecular complexes including an human beta secretase inhibitor binding pocket or beta secretase-like inhibitor binding pocket, as defined by the sets of structure coordinates described above.

TABLE 5

| Residues with 4Å of inhibitor binding site. | |
|---|---|
| GLY | 11 |
| GLY | 13 |
| LEU | 30 |
| ASP | 32 |
| GLY | 34 |
| SER | 35 |
| PRO | 70 |
| TYR | 71 |
| THR | 72 |
| GLN | 73 |
| PHE | 108 |
| ILE | 110 |
| TRP | 115 |
| ILE | 126 |
| TYR | 198 |
| ASP | 228 |

TABLE 5-continued

Residues with 4Å of inhibitor binding site.

| | |
|---|---|
| GLY | 230 |
| THR | 231 |
| THR | 232 |
| ARG | 235 |

TABLE 6

Residues with 7Å of inhibitor binding site.

| | |
|---|---|
| SER | 10 |
| GLY | 11 |
| GLN | 12 |
| GLY | 13 |
| TYR | 14 |
| LEU | 30 |
| VAL | 31 |
| ASP | 32 |
| THR | 33 |
| GLY | 34 |
| SER | 35 |
| SER | 36 |
| ASN | 37 |
| VAL | 69 |
| PRO | 70 |
| TYR | 71 |
| THR | 72 |
| GLN | 73 |
| GLY | 74 |
| LYS | 75 |
| TRP | 76 |
| ASP | 106 |
| LYS | 107 |
| PHE | 108 |
| PHE | 109 |
| ILE | 110 |
| TRP | 115 |
| ILE | 118 |
| ILE | 126 |
| ALA | 127 |
| ARG | 128 |
| TYR | 198 |
| LYS | 224 |
| ILE | 226 |
| ASP | 228 |
| SER | 229 |
| GLY | 230 |
| THR | 231 |
| THR | 232 |
| ASN | 233 |
| ARG | 235 |
| SER | 325 |
| THR | 329 |
| VAL | 332 |
| ALA | 335 |

TABLE 7

Residues with 10Å of inhibitor binding site.

| | |
|---|---|
| ARG | 7 |
| GLY | 8 |
| LYS | 9 |
| SER | 10 |
| GLY | 11 |
| GLN | 12 |
| GLY | 13 |
| TYR | 14 |
| TYR | 15 |
| ILE | 29 |
| LEU | 30 |
| VAL | 31 |
| ASP | 32 |

TABLE 7-continued

Residues with 10Å of inhibitor binding site.

| | |
|---|---|
| THR | 33 |
| GLY | 34 |
| SER | 35 |
| SER | 36 |
| ASN | 37 |
| ALA | 39 |
| TYR | 68 |
| VAL | 69 |
| PRO | 70 |
| TYR | 71 |
| THR | 72 |
| GLN | 73 |
| GLY | 74 |
| LYS | 75 |
| TRP | 76 |
| GLU | 77 |
| ILE | 102 |
| SER | 105 |
| ASP | 106 |
| LYS | 107 |
| PHE | 108 |
| PHE | 109 |
| ILE | 110 |
| ASN | 111 |
| SER | 113 |
| TRP | 115 |
| GLU | 116 |
| GLY | 117 |
| ILE | 118 |
| LEU | 119 |
| GLY | 120 |
| LEU | 121 |
| ALA | 122 |
| TYR | 123 |
| ALA | 124 |
| GLU | 125 |
| ILE | 126 |
| ALA | 127 |
| ARG | 128 |
| PRO | 129 |
| LEU | 154 |
| TRP | 197 |
| TYR | 198 |
| TYR | 199 |
| ASP | 223 |
| LYS | 224 |
| SER | 225 |
| ILE | 226 |
| VAL | 227 |
| ASP | 228 |
| SER | 229 |
| GLY | 230 |
| THR | 231 |
| THR | 232 |
| ASN | 233 |
| LEU | 234 |
| ARG | 235 |
| ARG | 307 |
| PHE | 322 |
| ALA | 323 |
| ILE | 324 |
| SER | 325 |
| GLN | 326 |
| SER | 327 |
| SER | 328 |
| THR | 329 |
| GLY | 330 |
| THR | 331 |
| VAL | 332 |
| MET | 333 |
| GLY | 334 |
| ALA | 335 |
| VAL | 336 |
| MET | 338 |
| GLU | 339 |

Three-Dimensional Configurations

X-ray structure coordinates define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes the scalable three-dimensional configuration of points derived from the structure coordinates of at least a portion of an human beta secretase molecule or molecular complex, as listed in Table 1, as well as structurally equivalent configurations, as described below. Preferably, the scalable three-dimensional configuration includes points derived from structure coordinates representing the locations of a plurality of the amino acids defining an human beta secretase inhibitor binding pocket.

In one embodiment, the scalable three-dimensional configuration includes points derived from structure coordinates representing the locations the backbone atoms of a plurality of amino acids defining the human beta secretase inhibitor binding pocket, preferably the amino acids listed in Table 5, more preferably the amino acids listed in Table 6, and most preferably the amino acids listed in Table 7. Alternatively, the scalable three-dimensional configuration includes points derived from structure coordinates representing the locations of the side chain and the backbone atoms (other than hydrogens) of a plurality of the amino acids defining the human beta secretase inhibitor binding pocket, preferably the amino acids listed in Table 5, more preferably the amino acids listed in Table 6, and most preferably the amino acids listed in Table 7.

Likewise, the invention also includes the scalable three-dimensional configuration of points derived from structure coordinates of molecules or molecular complexes that are structurally homologous to beta secretase, as well as structurally equivalent configurations. Structurally homologous molecules or molecular complexes are defined below. Advantageously, structurally homologous molecules can be identified using the structure coordinates of human beta secretase according to a method of the invention.

The configurations of points in space derived from structure coordinates according to the invention can be visualized as, for example, a holographic image, a stereodiagram, a model or a computer-displayed image, and the invention thus includes such images, diagrams or models.

Structurally Equivalent Crystal Structures

Various computational analyses can be used to determine whether a molecule or a inhibitor binding pocket portion thereof is "structurally equivalent," defined in terms of its three-dimensional structure, to all or part of human beta secretase or its inhibitor binding pockets. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention equivalent atoms are defined as protein backbone atoms (N, $C^\alpha$, C, and O) for all conserved residues between the two structures being compared. A conserved residue is defined as a residue which is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or inhibitor binding pocket thereof, or any portion thereof, that has a root mean square deviation of conserved residue backbone atoms (N, $C^\alpha$, C, O) of less than about 0.35 Å, when superimposed on the relevant backbone atoms described by the reference structure coordinates listed in Table 1, is considered "structurally equivalent" to the reference molecule. That is to say, the crystal structures of those portions of the two molecules are substantially identical, within acceptable error. Particularly preferred structurally equivalent molecules or molecular complexes are those that are defined by the entire set of structure coordinates listed in Table 1 ±a root mean square deviation from the conserved backbone atoms of those amino acids of not more than 0.35 Å. More preferably, the root mean square deviation is less than about 0.2 Å. Another embodiment of this invention is a molecular complex defined by the structure coordinates listed in Table 1 for those amino acids listed in Table 5, ±a root mean square deviation from the conserved backbone atoms of those amino acids of not more than 0.35 Å, preferably less than about 0.2 Å. Still another embodiment of this invention is a molecular complex defined by the structure coordinates listed in Table 1 for those amino acids listed in Table 6, ±a root mean square deviation from the conserved backbone atoms of those amino acids of not more than 0.35 Å, preferably less than about 0.2 Å.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of human beta secretase or a inhibitor binding pocket portion thereof, as defined by the structure coordinates of human beta secretase described herein.

Machine Readable Storage Media

Transformation of the structure coordinates for all or a portion of human beta secretase or the human beta secretase/ligand complex or one of its inhibitor binding pockets, for structurally homologous molecules as defined below, or for the structural equivalents of any of these molecules or molecular complexes as defined above, into three-dimensional graphical representations of the molecule or complex can be conveniently achieved through the use of commercially-available software.

The invention thus further provides a machine-readable storage medium including a data storage material encoded with machine readable data which, when using a machine programmed with instructions for using said data, is capable of displaying a graphical three-dimensional representation of any of the molecule or molecular complexes of this invention that have been described above. In a preferred embodiment, the machine-readable data storage medium includes a data storage material encoded with machine readable data which, when using a machine programmed with instructions for using said data, is capable of displaying a graphical three-dimensional representation of a molecule or molecular complex including all or any parts of an human beta secretase inhibitor binding pocket or an beta secretase-like inhibitor binding pocket, as defined above. In another preferred embodiment, the machine-readable data storage medium includes a data storage material encoded with machine readable data which, when using a machine programmed with instructions for using said data, is capable of displaying a graphical three-dimensional representation of a molecule or molecular complex defined by the structure coordinates of all of the amino acids listed in Table 1, ±a root mean square deviation from the backbone atoms of said amino acids of not more than 0.43 Å.

In an alternative embodiment, the machine-readable data storage medium includes a data storage material encoded with a first set of machine readable data which includes the Fourier transform of the structure coordinates set forth in Table 1, and which, when using a machine programmed with instructions for using said data, can be combined with a second set of machine readable data including the x-ray diffraction pattern of a molecule or molecular complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, track balls, touch pads, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of a binding pocket of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Structurally Homologous Molecules, Molecular Complexes, and Crystal Structures

The structure coordinates set forth in Table 1 can be used to aid in obtaining structural information about another crystallized molecule or molecular complex. The method of the invention allows determination of at least a portion of the three-dimensional structure of molecules or molecular complexes which contain one or more structural features that are similar to structural features of human beta secretase. These molecules are referred to herein as "structurally homologous" to human beta secretase. Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al., *FEMS Microbiol Lett* 174, 247–50 (1999), and available on world wide web at ncbi.nlm.nih.gov/gorf/b12.html. Preferably, the default values for all BLAST 2 search parameters are used, including matrix=BLOSUM62; open gap penalty=11, extension gap penalty =1, gap x_dropoff=50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with a native or recombinant amino acid sequence of human beta secretase (for example, SEQ ID NO: 1). More preferably, a protein that is structurally homologous to human beta secretase includes at least one contiguous stretch of at least 50 amino acids that shares at least 80% amino acid sequence identity with the analogous portion of the native or recombinant human beta secretase (for example, SEQ ID NO: 1)? Methods for generating structural information about the structurally homologous molecule or molecular complex are well-known and include, for example, molecular replacement techniques.

Therefore, in another embodiment this invention provides a method of utilizing molecular replacement to obtain structural information about a molecule or molecular complex whose structure is unknown including the steps of:

(a) crystallizing the molecule or molecular complex of unknown structure;

(b) generating an x-ray diffraction pattern from said crystallized molecule or molecular complex; and (c) applying at least a portion of the structure coordinates set forth in Table 1 to the x-ray diffraction pattern to generate a three-dimensional electron density map of the molecule or molecular complex whose structure is unknown.

By using molecular replacement, all or part of the structure coordinates of human beta secretase or the human beta secretase/ligand complex as provided by this invention can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of human beta secretase or the human beta secretase/inhibitor complex within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, "Use of the Rotation and Translation Functions," in *Meth. Enzymol.* 115, pp. 55–77 (1985); M. G. Rossman, ed., *The Molecular Replacement Method—A Collection of Papers on the Use of Non-Crystallographic Symmetry, Intl. Sci. Rev. Ser. No.* 13, Gordon & Breach, New York (1972)).

Structural information about a portion of any crystallized molecule or molecular complex that is sufficiently structurally homologous to a portion of human beta secretase can be resolved by this method. In addition to a molecule that shares one or more structural features with human beta secretase as described above, a molecule that has similar bioactivity, such as the same catalytic activity, substrate specificity or ligand binding activity as human beta secretase, may also be sufficiently structurally homologous to human beta secretase to permit use of the structure coordinates of human beta secretase to solve its crystal structure.

In a preferred embodiment, the method of molecular replacement is utilized to obtain structural information about a molecule or molecular complex, wherein the molecule or molecular complex includes at least one human beta secretase subunit or homolog. A "subunit" of human beta secretase is an human beta secretase molecule that has been truncated at the N-terminus or the C-terminus, or both. In the context of the present invention, a "homolog" of human beta secretase is a protein that contains one or more amino acid substitutions, deletions, additions, or rearrangements with respect to the amino acid sequence of human beta secretase (SEQ ID NO: 1), but that, when folded into its native conformation, exhibits or is reasonably expected to exhibit at least a portion of the tertiary (three-dimensional) structure of human beta secretase. For example, structurally homologous molecules can contain deletions or additions of one or more contiguous or noncontiguous amino acids, such as a loop or a domain. Structurally homologous molecules also include "modified" human beta secretase molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

A heavy atom derivative of human beta secretase is also included as an human beta secretase homolog. The term "heavy atom derivative" refers to derivatives of human beta secretase produced by chemically modifying a crystal of human beta secretase. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by x-ray diffraction analysis of the soaked crystal. This information, in turn, is used to generate the phase information used to construct three-dimensional structure of the protein (Blundell et al., *Protein Crystallography*, Academic Press (1976)).

Because human beta secretase can crystallize in more than one crystal form, the structure coordinates of human beta secretase as provided by this invention are particularly useful in solving the structure of other crystal forms of human beta secretase or human beta secretase complexes.

The structure coordinates of human beta secretase as provided by this invention are particularly useful in solving the structure of human beta secretase mutants. Mutants may be prepared, for example, by expression of human beta secretase cDNA previously altered in its coding sequence by oligonucleotide-directed mutagenesis. Mutants may also be generated by site-specific incorporation of unnatural amino acids into beta secretase proteins using the general biosynthetic method of Noren et al., *Science* 244:182–88 (1989). In this method, the codon encoding the amino acid of interest in wild-type human beta secretase is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant human beta secretase with the site-specific incorporated unnatural amino acid.

Selenocysteine or selenomethionine may be incorporated into wild-type or mutant human beta secretase by expression of human beta secretase-encoding cDNAs in auxotrophic *E. coli* strains (Hendrickson et al., *EMBO J.* 9:1665–72 (1990)). In this method, the wild-type or mutagenized human beta secretase cDNA may be expressed in a host organism on a growth medium depleted of either natural cysteine or methionine (or both) but enriched in selenocysteine or selenomethionine (or both). Alternatively, selenomethionine analogues may be prepared by down regulation methionine biosynthesis. (Benson et al., *Nat. Struct. Biol.* 2:644–53 (1995); Van Duyne et al., *J. Mol. Biol.* 229:105–24 (1993)).

The structure coordinates of human beta secretase listed in Table 1 are also particularly useful to solve the structure of crystals of human beta secretase, human beta secretase mutants or human beta secretase homologs co-complexed with a variety of chemical entities. This approach enables the determination of the optimal sites for interaction between chemical entities, including candidate human beta secretase inhibitors and human beta secretase. Potential sites for modification within the various binding site of the molecule can also be identified. This information provides an additional tool for determining the most efficient binding interactions, for example, increased hydrophobic interactions, between human beta secretase and a chemical entity. For example, high resolution x-ray diffraction data collected from crystals exposed to different types of solvent allows the determination of where each type of solvent molecule resides. Small molecules that bind tightly to those sites can then be designed and synthesized and tested for their human beta secretase inhibition activity.

All of the complexes referred to above may be studied using well-known x-ray diffraction techniques and may be refined versus 1.5–3.5 Å resolution x-ray data to an R value of about 0.30 or less using computer software, such as X-PLOR (Yale University, 81992, distributed by Molecular Simulations, Inc.; see, e.g., Blundell & Johnson, supra; *Meth. Enzymol.*, Vol. 114 & 115, H. W. Wyckoff et al., eds., Academic Press (1985)). This information may thus be used to optimize known human beta secretase inhibitors, and more importantly, to design new human beta secretase inhibitors.

The invention also includes the unique three-dimensional configuration defined by a set of points defined by the structure coordinates for a molecule or molecular complex structurally homologous to human beta secretase as determined using the method of the present invention, structurally equivalent configurations, and magnetic storage media including such set of structure coordinates.

Further, the invention includes structurally homologous molecules as identified using the method of the invention.

Homology Modeling

Using homology modeling, a computer model of an human beta secretase homolog can be built or refined without crystallizing the homolog. First, a preliminary model of the human beta secretase homolog is created by sequence alignment with human beta secretase, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. If the human beta secretase homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement including molecular dynamics calculations.

Rational Drug Design

Computational techniques can be used to screen, identify, select and/or design chemical entities capable of associating with human beta secretase or structurally homologous molecules. Knowledge of the structure coordinates for human beta secretase permits the design and/or identification of synthetic compounds and/or other molecules which have a shape complementary to the conformation of the human beta secretase binding site. In particular, computational techniques can be used to identify or design chemical entities, such as inhibitors, agonists and antagonists, that associate with an human beta secretase inhibitor binding pocket or an beta secretase-like inhibitor binding pocket. Inhibitors may bind to or interfere with all or a portion of an active site of human beta secretase, and can be competitive, non-competitive, or uncompetitive inhibitors; or interfere with dimerization by binding at the interface between the two monomers. Once identified and screened for biological activity, these inhibitors/agonists/antagonists may be used therapeutically or prophylactically to block human beta secretase activity and, thus, prevent the onset and/or further progression of Alzheimer's disease. Structure-activity data for analogues of ligands that bind to or interfere with human beta secretase or beta secretase-like inhibitor binding pockets can also be obtained computationally.

The term "chemical entity," as used herein, refers to chemical compounds, complexes of two or more chemical compounds, and fragments of such compounds or complexes. Chemical entities that are determined to associate with human beta secretase are potential drug candidates.

Data stored in a machine-readable storage medium that is capable of displaying a graphical three-dimensional representation of the structure of human beta secretase or a structurally homologous molecule, as identified herein, or portions thereof may thus be advantageously used for drug discovery. The structure coordinates of the chemical entity are used to generate a three-dimensional image that can be computationally fit to the three-dimensional image of human beta secretase or a structurally homologous molecule. The three-dimensional molecular structure encoded by the data in the data storage medium can then be computationally evaluated for its ability to associate with chemical entities. When the molecular structures encoded by the data is displayed in a graphical three-dimensional representation on a computer screen, the protein structure can also be visually inspected for potential association with chemical entities.

One embodiment of the method of drug design involves evaluating the potential association of a known chemical entity with human beta secretase or a structurally homologous molecule, particularly with an human beta secretase inhibitor binding pocket or beta secretase-like inhibitor binding pocket. The method of drug design thus includes computationally evaluating the potential of a selected chemical entity to associate with any of the molecules or molecular complexes set forth above. This method includes the steps of: (a) employing computational means to perform a fitting operation between the selected chemical entity and a inhibitor binding pocket or a pocket nearby the inhibitor binding pocket of the molecule or molecular complex; and (b) analyzing the results of said fitting operation to quantify the association between the chemical entity and the inhibitor binding pocket.

In another embodiment, the method of drug design involves computer-assisted design of chemical entities that associate with human beta secretase, its homologs, or portions thereof. Chemical entities can be designed in a stepwise fashion, one fragment at a time, or may be designed as a whole or "de novo."

To be a viable drug candidate, the chemical entity identified or designed according to the method must be capable of structurally associating with at least part of an human beta secretase or beta secretase-like inhibitor binding pockets, and must be able, sterically and energetically, to assume a conformation that allows it to associate with the human beta secretase or beta secretase-like inhibitor binding pocket. Non-covalent molecular interactions important in this association include hydrogen bonding, van der Waals interactions, hydrophobic interactions, and electrostatic interactions. Conformational considerations include the overall three-dimensional structure and orientation of the chemical entity in relation to the inhibitor binding pocket, and the spacing between various functional groups of an entity that directly interact with the beta secretase-like inhibitor binding pocket or homologs thereof.

Optionally, the potential binding of a chemical entity to an human beta secretase or beta secretase-like inhibitor binding pocket is analyzed using computer modeling techniques prior to the actual synthesis and testing of the chemical entity. If these computational experiments suggest insufficient interaction and association between it and the human beta secretase or beta secretase-like inhibitor binding pocket, testing of the entity is obviated. However, if computer modeling indicates a strong interaction, the molecule may then be synthesized and tested for its ability to bind to or interfere with an human beta secretase or beta secretase-like inhibitor binding pocket. Binding assays to determine if a compound actually interferes with human beta secretase can also be performed and are well known in the art. Binding assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

One skilled in the art may use one of several methods to screen chemical entities or fragments for their ability to associate with an human beta secretase or beta secretase-like inhibitor binding pocket. This process may begin by visual inspection of, for example, an human beta secretase or beta secretase-like inhibitor binding pocket on the computer screen based on the human beta secretase structure coordinates listed in Table 1 or other coordinates which define a similar shape generated from the machine-readable storage medium. Selected fragments or chemical entities may then be positioned in a variety of orientations, or docked, within the inhibitor binding pocket. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical entities. Examples include GRID (Goodford, *J. Med. Chem.* 28:849–57 (1985); available from Oxford University, Oxford, UK); MCSS (Miranker et al., *Proteins: Struct. Funct. Gen.* 11:29–34 (1991); available from Molecular Simulations, San Diego, Calif.); AUTODOCK (Goodsell et al., *Proteins: Struct. Funct. Genet.* 8:195–202 (1990); available from Scripps Research Institute, La Jolla, Calif.); and DOCK (Kuntz et al., *J. Mol. Biol.* 161:269–88 (1982); available from University of California, San Francisco, Calif.).

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of human beta secretase. This would be followed by manual model building using software such as QUANTA or SYBYL (Tripos Associates, St. Louis, Mo.).

Useful programs to aid one of skill in the art in connecting the individual chemical entities or fragments include, without limitation, CAVEAT (Bartlett et al., in "*Molecular Recognition: Chemical and Biological Problems*," Special Publ., Royal Chem. Soc., 78:182–96 (1989); Lauri et al., *J. Comput. Aided Mol. Des.* 8:51–66 (1994); available from the University of California, Berkeley, Calif.); 3D database systems such as ISIS (available from MDL Information Systems, San Leandro, Calif.; reviewed in Martin, *J. Med. Chem.* 35:2145–54 (1992)); and HOOK (Eisen et al., *Proteins: Struc., Funct., Genet.* 19:199–221 (1994); available from Molecular Simulations, San Diego, Calif.).

Human beta secretase binding compounds may be designed "de novo" using either an empty binding site or optionally including some portion(s) of a known inhibitor(s). There are many de novo ligand design methods including, without limitation, LUDI (Böhm, *J. Comp. Aid. Molec. Design.* 6:61–78 (1992); available from Molecular Simulations Inc., San Diego, Calif.); LEGEND (Nishibata et al., *Tetrahedron*, 47:8985 (1991); available from Molecular Simulations Inc., San Diego, Calif.); LeapFrog (available from Tripos Associates, St. Louis, Mo.); and SPROUT (Gillet et al., *J. Comput. Aided Mol. Design* 7:127–53 (1993); available from the University of Leeds, UK).

Once a compound has been designed or selected by the above methods, the efficiency with which that entity may bind to or interfere with an human beta secretase or beta secretase-like inhibitor binding pocket may be tested and optimized by computational evaluation. For example, an effective human beta secretase or beta secretase-like inhibitor binding pocket inhibitor must preferably demonstrate a relatively small difference in energy between its bound and free states (i.e., a small deformation energy of binding). Thus, the most efficient human beta secretase or beta secretase-like inhibitor binding pocket inhibitors should preferably be designed with a deformation energy of binding of not greater than about 10 kcal/mole; more preferably, not greater than 7 kcal/mole. human beta secretase or beta secretase-like inhibitor binding pocket inhibitors may interact with the inhibitor binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to or interfering with an human beta secretase or beta secretase-like inhibitor binding pocket may be further computationally optimized so that in its bound state it would preferably lack repulsive electrostatic interaction with the target enzyme and with the surrounding water molecules. Such non-complementary electrostatic interactions include repulsive charge—charge, dipole—dipole, and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. 81995); AMBER, version 4.1 (P. A. Kollman, University of California at San Francisco, 81995); QUANTA/CHARMM (Molecular Simulations, Inc., San Diego, Calif. 81995); Insight II/Discover (Molecular Simulations, Inc., San Diego, Calif. 81995); DelPhi (Molecular Simulations, Inc., San Diego, Calif. 81995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach encompassed by this invention is the computational screening of small molecule databases for chemical entities or compounds that can bind in whole, or in part, to a human beta secretase or beta secretase-like inhibitor binding pocket. In this screening, the quality of fit of such entities to the binding site may be judged either by shape complementarity or by estimated interaction energy (Meng et al., *J. Comp. Chem.* 13:505–24 (1992)).

This invention also enables the development of chemical entities that can isomerize to short-lived reaction intermediates in the chemical reaction of a substrate or other compound that interferes with or with human beta secretase. Time-dependent analysis of structural changes in human beta secretase during its interaction with other molecules is carried out. The reaction intermediates of human beta secretase can also be deduced from the reaction product in co-complex with human beta secretase. Such information is useful to design improved analogues of known human beta secretase inhibitors or to design novel classes of inhibitors based on the reaction intermediates of the human beta secretase and inhibitor co-complex. This provides a novel route for designing human beta secretase inhibitors with both high specificity and stability.

Yet another approach to rational drug design involves probing the human beta secretase crystal of the invention with molecules including a variety of different functional groups to determine optimal sites for interaction between candidate human beta secretase inhibitors and the protein. For example, high resolution x-ray diffraction data collected from crystals soaked in or co-crystallized with other molecules allows the determination of where each type of solvent molecule sticks. Molecules that bind tightly to those sites can then be further modified and synthesized and tested for their beta secretase inhibitor activity (Travis, *Science* 262:1374 (1993)).

In a related approach, iterative drug design is used to identify inhibitors of human beta secretase. Iterative drug design is a method for optimizing associations between a protein and a compound by determining and evaluating the three-dimensional structures of successive sets of protein/compound complexes. In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

A compound that is identified or designed as a result of any of these methods can be obtained (or synthesized) and tested for its biological activity, e.g., inhibition of beta secretase activity.

Pharmaceutical Compositions (Inhibitors)

Pharmaceutical compositions of this invention include an inhibitor of human beta secretase activity identified according to the invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Optionally, the pH of the formulation is adjusted with pharmaceutically acceptable acids, bases, or buffers to enhance the stability of the formulated compound or its delivery form.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. Oral administration or administration by injection is preferred. The term parenteral as used herein includes subcutaneous, intracutaneous, intravenous, intramuscular, intraarticular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the human beta secretase inhibitory compounds described herein are useful for the prevention and treatment of human beta secretase mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

In order that this invention be more fully understood, the following examples are set forth. These examples are for the purpose of illustration only and are not to be construed as limiting the scope of the invention in any way.

EXAMPLES

Crystallization and Structure Determination of Human Beta Secretase

A. Expression, Purification, and Crystallization

Expression and Purification of Beta Secretase from HEK 293 Cells.

The expression plasmid=pcDNA3.1/myc/his (neomycin) (Invitrogen) contains beta secretase extending from Met [−21] to Ser [432] with a myc tag followed by a hexahistidine tag [EQKLISEEDLNMHTEHHHHHH*] (SEQ ID NO:2) at the C-terminus. Following transfection in HEK293 cells, stable cells were selected using 0.8 mg/ml G418. A stable clone of transfected HEK293 cells that secretes human beta-secretase was expanded in static, monolayer cell culture. Confluent cultures were detached by shaking and a plurality of plastic, 225 cm² T-flasks were each inoculated with a suspension of 1–5×106 cells in 100 ml of High-Glucose Dulbecco's Modified Eagle medium that was supplemented with 5% fetal bovine serum and 500 micrograms/ml G418. These cell cultures were incubated in a humidified. 37° C. incubator gassed with 95% air and 5% $CO_2$. Once the cells reached confluence the growth medium in each flask was removed and replaced with 100 ml fresh medium. The conditioned, culture medium supernatant was harvested aseptically and replaced by fresh medium every 48–72 hours. The harvested medium was pooled, centrifuged at 1000×g to remove cell debris, and was stored in plastic bottles at 4° C. Cell monolayers were maintained in semi-continuous culture for several weeks until the cells either began to die or to detach from the culture flasks. The cells were then resuspended and used to inoculate a fresh set of production flasks.

For purification, the medium was concentrated approximately 10-fold using a tangential flow concentrator equipped with a 30,000 molecular weight cutoff cartridge. Solid ammonium sulfate was then slowly added with stirring to the concentrate at 4° C. to a final value of 40% saturation (242 g/L). After stirring at 4° C. for 30 minutes, the suspension was clarified by centrifugation (16,000×g, 60 minutes) and the supernatant taken for further analysis. The 40% ammonium sulfate supernatant was adjusted to 80% saturation by slow addition of solid ammonium sulfate with stirring at 4° C. (281 g/L). After stirring for 30 minutes at 4° C., the insoluble material was collected by centrifugation as indicated above and the 40–80% ammonium sulfate pellet taken for further analysis.

Figure 2:
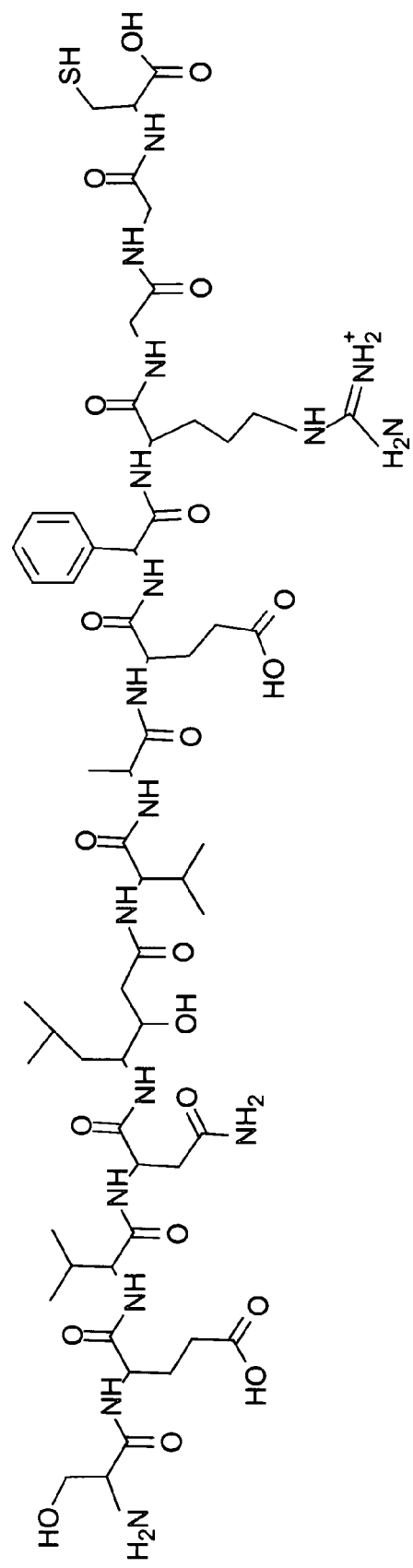
FIG. 2 is the synthetic peptide Ser-Glu-Val-Asn-Sta-Val-Ala-Glu-Phe-Arg-Gly-Gly-Cys (where Sta=statine) (SEQ ID NO:3), PNU-292593E, used for affinity purification of beta secretase.
Figure 3:
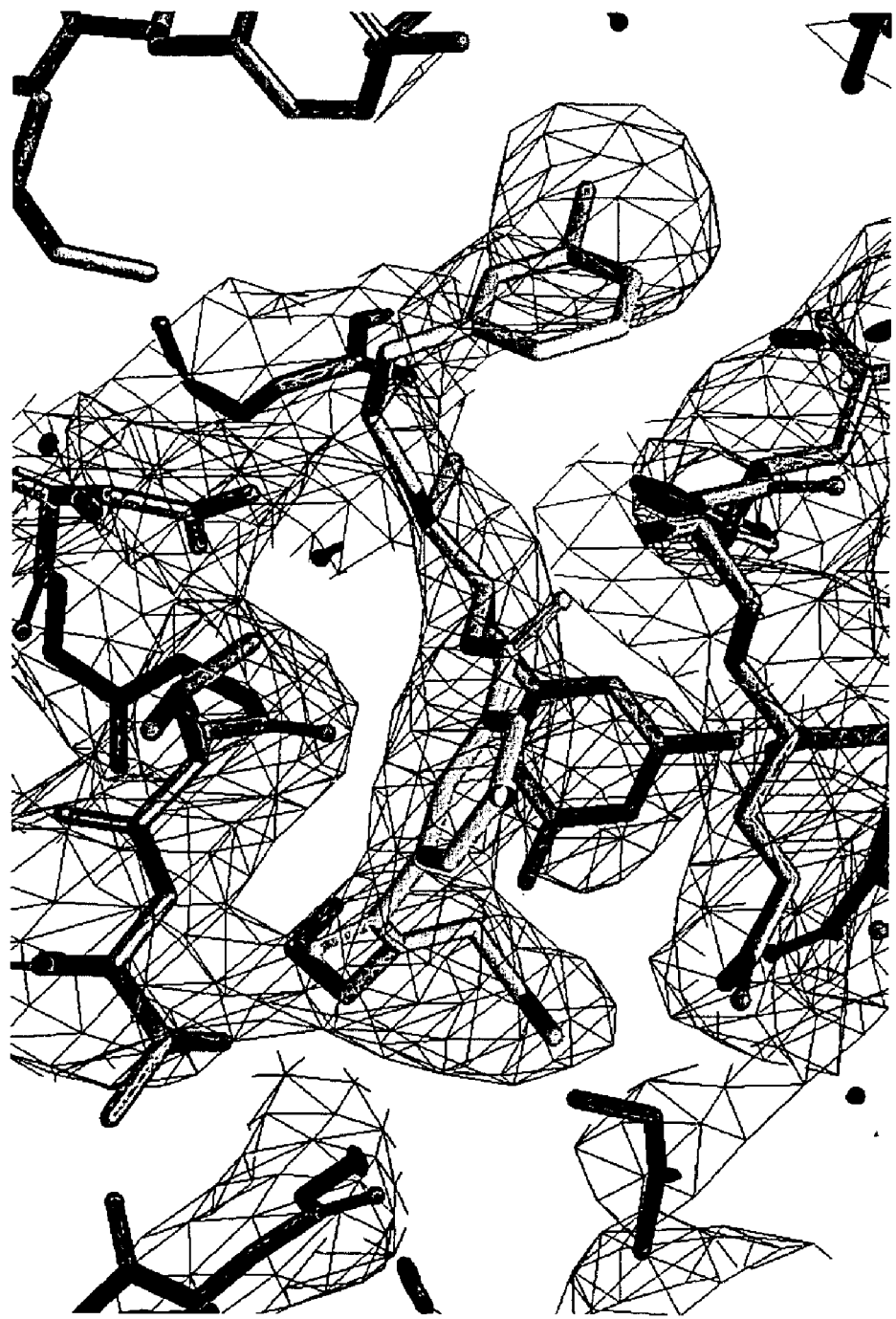
FIG. 3 is an electron density map for the inhibitor illustrated in FIG. 1 at 3.2 Å.
Figure 4:
FIG. 4 is a stereo view of a $C^\alpha$ trace of human beta secretase (black line) in the presence of the inhibitor illustrated in FIG. 1. The general location of the inhibitor trace (gray line) is indicated by an arrow.
Figure 4:
Figure 5:
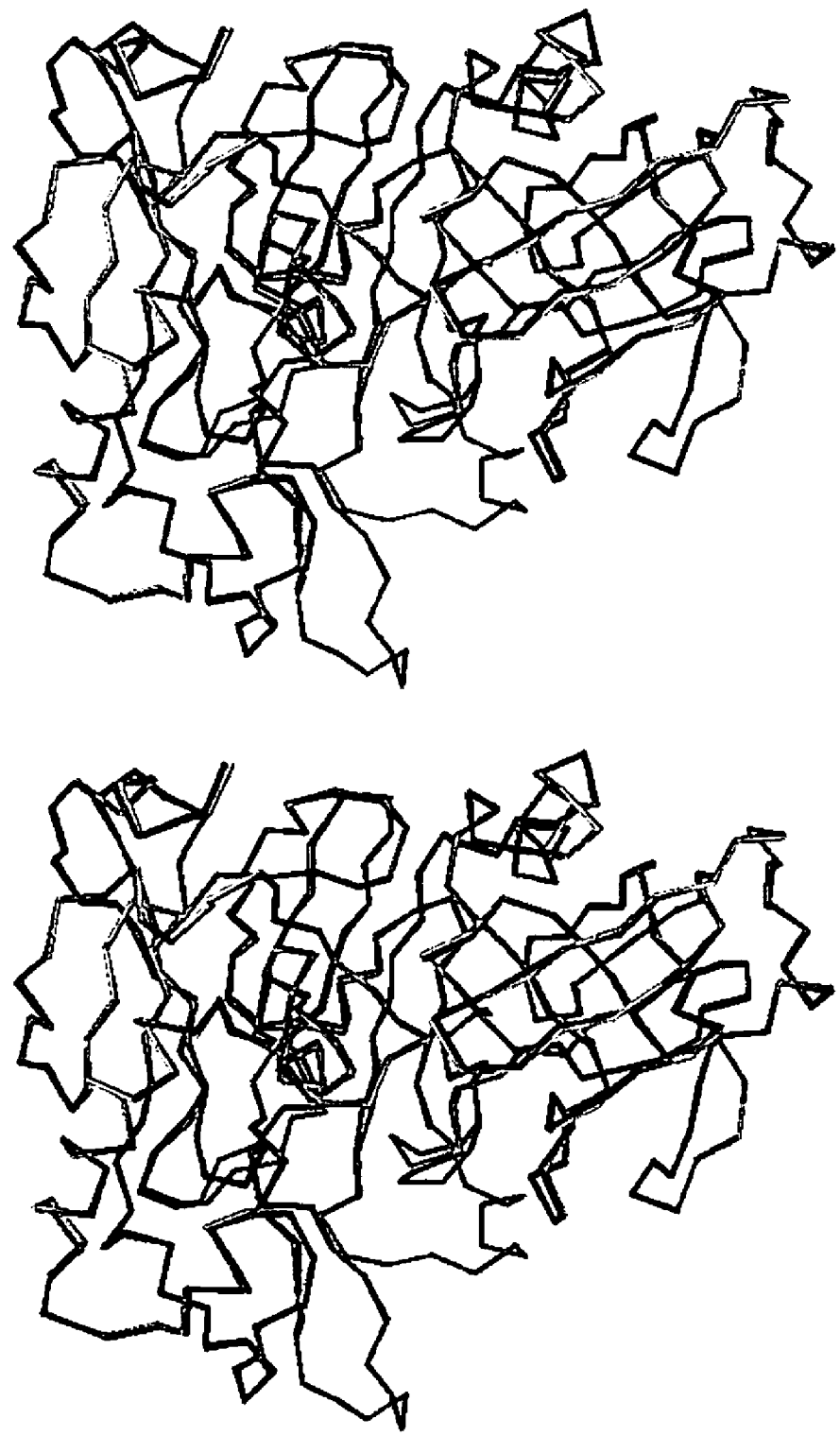
FIG. 5 is a stereo view of $C^\alpha$ traces of human beta secretase as a superposition of a data set from the present invention (black line) with a data set from Hong et al, Science 290:150–53 (2000) (gray line). The r.m.s. deviation on $C^\alpha$ between the illustrated data sets was 0.43 Å.
Figure 6:
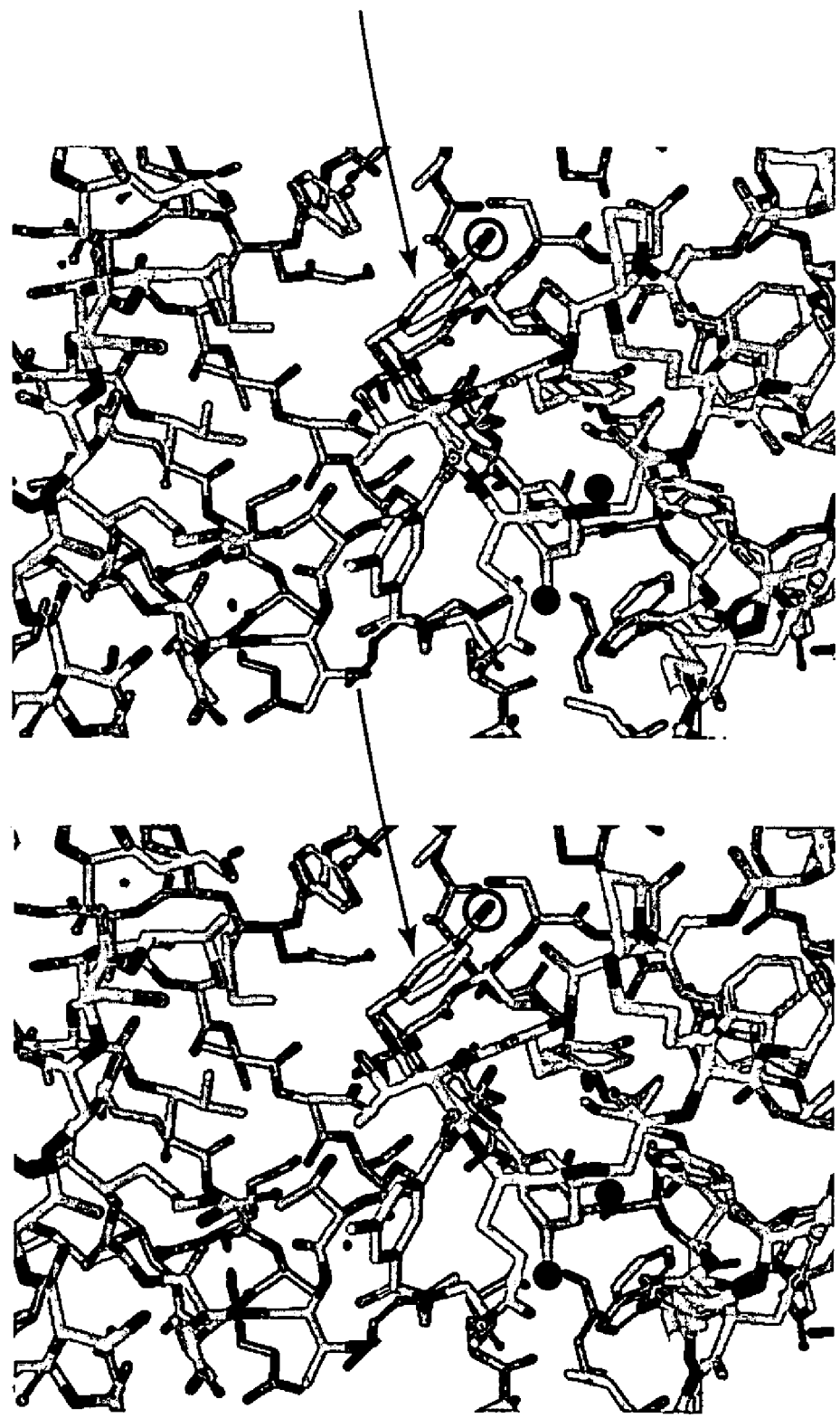
FIG. 6 depicts a stereo view of the active site of human beta secretase (illustrated with light gray carbons, dark gray oxygens, and black nitrogens) with the inhibitor illustrated in FIG. 1. The general location of the inhibitor is indicated by an arrow (illustrated with light gray carbons, dark gray oxygens, and black nitrogens). The iodine atom is circled and the two fluorine atoms are indicated by a "●" symbol.

The 40–80% ammonium sulfate pellet was dissolved in 25 mM Tris-HCl (8.5)/0.5 M NaCl/10 mM imidazole (1/10 the original volume) and applied to a 12.5 ml column containing Ni⁺-NTA Fast Flow resin previously equilibrated in the same buffer. Following sample application, the column was washed with 10 column volumes of loading buffer and then eluted with 25 mM Tris-HCl (8.5)/0.5 M NaCl/50 mM imidazole. The material eluting in 50 mM imidazole was pooled, concentrated approximately 10-fold using a YM 30 membrane (30,000 MWCO), and then dialyzed against 10 mM HEPES-Na (8.0) using 50,000 molecular weight cutoff tubing. For affinity purification, the synthetic peptide Ser-Glu-Val-Asn-Sta-Val-Ala-Glu-Phe-Arg-Gly-Gly-Cys (where Sta=statine, PNU-292593E, SEQ ID NO:3, the structure being illustrated in FIG. 2) was synthesized and coupled to sulfolink resin (Pierce Chemical Company) as recommended by the manufacture. The dialyzed material from above was adjusted to 0.1 M NaOAc (4.5) by addition of 1/10 volume of 1.0 M NaOAc (4.5) and immediately applied to the PNU-292593E/sulfolink column (6 ml containing 1.0 mg PNU-292593/ml of resin) that had been previously equilibrated in 25 mM NaOAc (4.5). Following sample application, the column was washed with 10 column volumes of 25 mM NaOAc (4.5) and then eluted with 50 mM $NaBO_3$ (8.5). N-terminal sequence analysis of the affinity purified material revealed an equimolar mixture of pro- and processed human beta-secretase beginning at $Thr^1$ and $Glu^{25}$ respectively. The final protein concentration was determined by amino acid analysis assuming a 60 kDa glycoprotein.

Production of Recombinant Human β-Secretase in Insect sf9 Cells and CHO-K1 Cells. The coding sequence was engineered to delete the terminal transmembrane and cytoplasmic domain and introduce a C-terminal hexahistidine tag using the polymerase chain reaction. The 5' sense oligonucleotide primer [CGCTTTGGATCCGTGGA-CAACCTGAGGGGCAA] (SEQ ID NO:4) was designed to incorporate a BamHI site for ease in subcloning and Kozak consensus sequence around the initiator methionine for optimal translation initiation. The 3' antisense primer [CGCTTTGGTACCCTATGACTCATCT-GTCTGTGGAATGTTG] (SEQ ID NO:5) incorporated a hexahistidine tag and translation termination codon just upstream of the predicted transmembrane domain ($Ser^{432}$) and a NotI restriction site for cloning. The PCR was performed on the plasmid template pcDNA3.1 hygroAsp2R for 15 cycles [94° C., 30 sec., 65° C., 30 sec., 72° C., 30 sec] using Pwo I polymerase (Roche Biochemicals, Indianapolis, Ind.) as outlined by the manufacturer. The PCR product was digested to completion with BamHI and NotI and ligated into the BamHI and NotI sites of the Baculovirus transfer vector pVL1393 (PharMingen, San Diego, Calif.). A portion of the ligation was used to transform competent E. coli DH5α cells and recombinant clones were selected on ampicillin. Individual clones containing the proper cDNA inserts were identified by PCR. Plasmid DNA from clone (pVL1393/Hu_Asp-2LΔTM(His)$_6$) was prepared by alkaline lysis and banding in CsCl. The integrity of the insert was confirmed by complete DNA sequencing. For CHO-K1 cell expression, plasmid pVL1393/Hu_Asp-2LΔTM(His)$_6$ was digested with BamHI and NotI and the resulting fragment subcloned into the mammalian expression vector pcDNA3.1 (hygro) as described above to yield pcDNA3.1 (hygro)/Hu_Asp-2LΔTM(His)$_6$).

For expression, CHO-K1 cells (50% confluent) were transfected with cationic liposome/pcDNA3.1 (hygro)/Hu-Asp-2LΔTM(His)$_6$ complexes in α-MEM medium containing 10% FBS overnight. Selection was performed in the same medium containing 0.5 mg/L hygromycin B for seven days and surviving cells were cloned by limiting dilution. Eight cell lines were screened for soluble β-secretase by Western blot analysis using a polyclonal rabbit antiserum specific for human β-secretase (UP-191). Conditioned medium from each clonal cell line was concentrated by Ni⁺-NTA chromatography and the histidine-tagged polypeptide eluted with buffer containing 50 mM imidazole. Aliquots of the latter fraction were displayed on a PVDF membrane and recombinant soluble human β-secretase was visualized using UP-191 antiserum and alkaline phosphatase conjugated goat antirabbit second antibody. Based on these results, clone #4 showed the highest expression level and was used for all subsequent experiments.

For Baculovirus expression (BVES), recombinant virus containing the coding sequence of soluble β-secretase was isolated following recombination of the plasmid transfer vector pVL1393/Hu_Asp-2LΔTM(His)$_6$ in sf9 cells using standard methods. Individual virus isolates were used to infect sf9 cells and expression of the desired polypeptide was quantified by Western blot analysis of the conditioned medium collected 69 hr post infection as described above. The recombinant virus directing the synthesis of the highest level of β-secretase was scaled-up for protein production.

For production of soluble α-secretase in insect cells, sf9 cells were infected with recombinant Baculovirus at a multiplicity of infection of 1.0 in serum free medium and conditioned medium harvested 69 hours post-infection. For CHO cells, the production cell line expressing secreted soluble human β-secretase was expanded in either roller bottles or in a packed-bed bioreactor in medium containing 0.5 fetal bovine serum. Conditioned medium was collected and stored at 4° C. until processing.

Purification of Recombinant Human βSecretase from BVES or CHO-K1 Cells. For purification from either source, the medium was concentrated approximately 10-fold using a tangential flow concentrator equip with a 30,000 molecular weight cutoff cartridge. Solid ammonium sulfate was then slowly added with stirring to the concentrate at 4° C. to a final value of 40% saturation (242 g/L). After stirring at 4° C. for 30 minutes, the suspension was clarified by centrifugation (16,000×g, 60 minutes) and the supernatant taken for further analysis. The 40% ammonium sulfate supernatant was adjusted to 80% saturation by slow addition of solid ammonium sulfate with stirring at 4° C. (281 g/L). After stirring for 30 minutes at 4° C., the insoluble material was collected by centrifugation as indicated above and the 40–80% ammonium sulfate pellet taken for further analysis.

The 40–80% ammonium sulfate pellet was dissolved in 25 mM Tris-HCl (8.5)/0.5 M NaCl 0 mM imidazole (1/10 the original volume) and applied to a 12.5 ml column containing Ni$^+$-NTA Fast Flow resin previously equilibrated in the same buffer. Following sample application, the column was washed with 10 column volumes of loading buffer and then eluted with 25 mM Tris-HCl (8.5)/0.5 M NaCl/50 mM imidazole. The material eluting in 50 mM imidazole was pooled, concentrated approximately 10-fold using a YM 30 membrane (30,000 MWCO), and then dialyzed against 10 mM HEPES-Na (8.0) using 50,000 molecular weight cutoff tubing. For affinity purification, the synthetic peptide Ser-Glu-Val-Asn-Sta-Val-Ala-Glu-Phe-Arg-Gly-Gly-Cys (where Sta=statine, PNU-292593E) (SEQ ID NO:3) was synthesized and coupled to sulfolink resin (Pierce Chemical Company) as recommended by the manufacture. The dialyzed material from above was adjusted to 0.1 M NaOAc (4.5) by addition of 1/10 volume of 1.0 M NaOAc (4.5) and immediately applied to the PNU-292593E/sulfolink column (6 ml containing 1.0 mg PNU-292593/ml of resin) that had been previously equilibrated in 25 mM NaOAc (4.5). Following sample application, the column was washed with 10 column volumes of 25 mM NaOAc (4.5) and then eluted with 50 mM NaBO$_3$ (8.5). N-terminal sequence analysis of the affinity purified material revealed an equimolar mixture of pro- and processed human α-secretase beginning at Thr$^1$ and Glu$^{25}$, respectively. The final protein concentration was determined by amino acid analysis assuming a 52 kDa glycoprotein for insect cells and a 60 kDa glycoprotein for CHO cells, respectively.

Protein Crystallization. Based on observations of the initial screening effort, fresh protein derived from CHO cells was concentrated to 42 mg/ml and mixed with a new inhibitor (FIG. 1) so that the final concentration of the mix was 40 mg/ml beta secretase, and 2 mM of the inhibitor shown in FIG. 1, in 20 mM Hepes pH 7.8, 10% DMSO. This preparation was screened with Hampton Screen 1 (Hampton Research, Laguna Nigel, Calif.) and Wizard Screen 1 (Emerald Biostructures, Bainbridge Island, Wash.) at room temperature (20° C.). 500-mL well volumes were used. A 1: 1 ratio of protein-compound mix to the well solution was used in a hanging drop format to complete the screen. After 10 days, but less than 18 days later crystals were observed in Wizard Screen 1, Condition No. 45 (20% PEG 3000, 0.1M NaOAc-pH 4.5). Optimization and seeding efforts around this condition provided crystals that grew in 17–20% PEG 3000, 0.1M Na Acetate pH 4.5. Seeding was done utilizing a cat whisker which was touched to a drop containing microcrystals and stepwise diluted by streaking through one row of the optimization tray. Cross-seeding efforts provided crystals of HEK 293 cell derived protein (38 mg/ml in 20 mM Hepes pH 7.8, 50 mM NaCl, 10% DMSO, 2 mM of the inhibitor shown in FIG. 1 from CHO cell derived seed stock. Macroseeding by moving small crystals with a loop from the target drop to a fresh drop containing 17–20% PEG3000, 0.1 M Na Acetate pH 4.5 also resulted in crystals that doubled or more in size, usually with a shower of microcrystals also. Crystals were obtained in hanging drop or sitting drop methods by seeding. Crystals obtained from streak seeding attempts were frozen in a cryoprotectant solution based on the mother liquor plus 20% Ethylene Glycol. The crystals were then soaked incrementally through 5% intervals of the cryoprotectant in 3 to 5-minute intervals. Crystals have also been grown in the presence of 10% glycerol or 10% ethylene glycol to facilitate stabilization into cryogenic solutions. In these cases, the crystals were soaked incrementally through 5% intervals of the cryoprotectant in 3 to 5-minute intervals. The use of other cryo agents would be apparent to one of skill in the art.

Fresh Asp2 protein derived from Baculovirus cells (BVES) was concentrated to 18.6 mg/mL and mixed with the inhibitor illustrated in FIG. 1, so that the final concentration of the mix was 18 mg/mL beta secretase and 2 mM of the inhibitor illustrated in FIG. 1 in 20 mM Hepes pH 7.8 with 5% DMSO. Observations of how CHO derived Asp2 crystallized led to the following crystallization effort for BVES Asp2. A PEG range from 17–22% PEG 3000, 0.1M sodium acetate pH 4.5, with none, 10% DMSO, or 10% glycerol was used in 1000 µL wells. Sample drops were streak seeded at set up, with $10^{-1}$ seed dilution of CHO seed stocks as described above. A crystal measuring 1.0×0.1×0.1 mm$^3$ was obtained in 17% PEG 3000, 0.1M sodium acetate pH 4.5 with 10% DMSO, and 3 days post set up. Crystals were incrementally soaked into a cryoprotectant solution containing a final concentration of 20% DMSO in 5 minute intervals.

B. X-ray Diffraction Characterization for Beta Secretase Expressed in CHO Cells

All data collection was carried out at the Advanced Photon Source (Argonne, Ill.) at beamline 17-ID. The crystals diffracted to 3.2A using synchrotron radiation. Crystals were of the space group P3$_2$21 with cell constants a=112±20 Å, b=112±20 Å, c=110±20 Å, α=β=90°, γ=120°. The Matthews coefficient for these crystals assuming that there is one molecules in the asymmetric unit is 3.5 Å/Da with 65% solvent. The structure determination (see below) revealed the presence of electron density in the active site appropriate for the inhibitor shown in FIG. 1

C. Molecular Replacement for Beta Secretase Expressed in CHO Cells

A molecular replacement solution was determined using AMORE (Navaza, *Acta Cryst.*, D50:157–63 (1994); Collaborative Computational Project N4, *Acta Cryst.* D50: 760–3 (1994))) by utilizing a previously published model of human beta secretase, 1FKN, (Hong et al., *Science* 290:150-53 (2000)) made available from the Protein Data Bank on the world wide web at rcsb.org. Using the 1FKN model, the initial rotation solution gave a single strong peak of 9.7σ with the next strongest peak appearing at 4.0σ. The final determination of the space group (P321, P3$_1$21, or P3$_2$21) was determined experimentally by testing translation searches in each space group. A translation search in the correct space group, P3$_2$21, resulted in a correlation coefficient of 55.1 with an R-factor of 39.9% to 4 Å resolution.

TABLE 8

Data collection statistics for structure of Human Beta Secretase
(data collected at λ 1.0000 Å at APS, 17-ID)

| Resolution Range | $R_{sym}$ |
|---|---|
| 20–6.81 | 0.048 |
| 6.81–5.44 | 0.095 |
| 5.44–4.77 | 0.112 |
| 4.77–4.33 | 0.113 |
| 4.33–4.03 | 0.181 |
| 4.03–3.79 | 0.224 |
| 3.79–3.60 | 0.248 |
| 3.60–3.45 | 0.288 |
| 3.45–3.31 | 0.321 |
| 3.31–3.20 | 0.324 |
| All reflections | 0.098 |

D. Model Building and Refinement for Beta Secretase Expressed in CHO Cells

Further rigid body refinement of the model in CNX (Molecular Simulations, Inc) followed by minimization and group b-factor refinement gave an R-factor of 35.1% and a Free R-factor of 37.7% to 3.2 Å. During each cycle of refinement a bulk solvent correction was incorporated (Jiang et al., *J. Mol. Biol.* 243:100–15 (1994)). Progress of the refinement was monitored by a decrease in both the R-factor and Free R-factor.

At this point, inspection of the electron density map within the active site revealed electron density that was unaccounted for by the protein model and consistent with the shape of the inhibitor shown in FIG. 1 that was present in the crystallization conditions. Model building was done using the program CHAIN (Sack, Journal of Molecular Graphics 6:224–25 (1988)) and LORE (Finzel, Meth. Enzymol. 277:230–42 (1997)). Modest rebuilding of the model into the 3.2 Å low resolution map afforded the opportunity for further cycles of refinement giving improvement of the R-factor to 31.6% and a Free R-factor of 35.7%. Finally, the inhibitor was included in the refinement to give the current R-factor of 29.9% and a Free R-factor of 34.9%.

Inspection of the electron density throughout the molecule indicates that all three disulfide bonds are intact (Cys155-Cys359,Cys217-Cys382, and Cys269-Cys319). In addition, the electron density near Asn92, Ans162, and Asn293, indicates the presence of glycosylation. Only the glycosylation at Asn111 is disordered enough not to be visible in the electron density map. Residues 158–170 and 311 to 317 were disordered in the electron density and therefore have been omitted from the model.

TABLE 9

Refinement Statistics for structure of Human Beta Secretase

| | R-factor | Free R-factor | No. of reflections |
|---|---|---|---|
| 20–3.2 Å F≧2σ | 0.2991 | 0.3483 | 9883 |

| | Bonds (Å) | Angles(°) |
|---|---|---|
| r.m.s deviation from ideal geometry | 0.012 | 1.7 |

| | Number of atoms | Average B-factor |
|---|---|---|
| Protein | 2880 | 65.24 |
| Waters | 41 | 74.89 |
| Total | 2921 | 65.38 |

E. X-ray Diffraction Characterization for Baculovirus Produced Human Beta Secretase Crystals.

All data collection was carried out at the Advanced Photon Source (Argonne, Ill.) at beamline 17-ID. The crystals diffracted to 2.7 Å using synchrotron radiation. Crystals were of the space group $P3_221$ with cell constants a=99.4±35 Å, b=99.4±35 Å, c=117±35 Å, α=β=90°, γ120°. The Matthews coefficient for these crystals assuming that there is one molecule in the asymmetric unit is 2.9 Å/Da with 58% solvent. The structure determination (see below) revealed the presence of electron density in the active site appropriate for the inhibitor shown in FIG. 1.

F. Molecular Replacement for Baculovirus Produced Human Beta Secretase Crystals.

A molecular replacement solution was determined using AMORE (Navaza 1994; Collaborative Computational Project N4, *Acta Cryst.* D50:760–3 (1994))) by utilizing the structure of human beta secretase produced from CHO cells. Using the CHO beta secretase model, the initial rotation solution gave a strong peak of 10.2% with the next strongest peak appearing at 8.0%. The space group was $P3_221$. A translation search in the correct space group, $P3_221$, resulted in a correlation coefficient of 57.8 with an R-factor of 41.5% to 4 Å resolution.

TABLE 10

Data collection statistics for structure of Human Beta Secretase
expressed in a Baculovirus expression system (data collected at
λ 1.0000 Å at APS, 17-ID)

| Resolution Range | $R_{sym}$ |
|---|---|
| 99.0–5.81 | 0.045 |
| 5.81–4.61 | 0.076 |
| 4.61–4.03 | 0.093 |
| 4.03–3.66 | 0.117 |
| 3.66–3.40 | 0.139 |
| 3.40–3.19 | 0.176 |
| 3.19–3.03 | 0.149 |
| 3.03–2.90 | 0.174 |
| 2.90–2.79 | 0.169 |
| 2.79–2.69 | 0.273 |
| All reflections | 0.073 |

G. Model Building and Refinement for Baculovirus Produced Human Beta Secretase Crystals.

Further rigid body refinement of the model in CNX (Molecular Simulations, Inc) followed by minimization refinement gave an R-factor of 36.4% to 2.7 Å. During each cycle of refinement a bulk solvent correction was incorporated (Jiang et al., *J. Mol. Biol.* 243:100–15 (1994)).

At this point, inspection of the electron density map within the active site revealed electron density that was unaccounted for by the protein model and consistent with the shape of the inhibitor illustrated in FIG. 1, that was present in the crystallization conditions. Model building was done using the program CHAIN (Sack, *Journal of Molecular Graphics* 6:224–25 (1988)) and LORE (Finzel, *Meth. Enzymol.* 277:230–42 (1997)).

The complete disclosure of all patents, patent applications including provisional applications, and publications, and electronically available material (e.g., GenBank amino acid and nucleotide sequence submissions) cited herein are incorporated by reference. The foregoing detailed description and examples have been given for clarity of understanding only.

No unnecessary limitations are to be understood therefrom. The invention is not limited to the exact details shown and described; many variations will be apparent to one skilled in the art and are intended to be included within the invention defined by the claims.

SEQUENCE LISTING FREE TEXT

SEQ ID NO: 1 residues for recombinant human beta secretase present in the X-ray structure

What is claimed is:

1. A crystal of beta secretase co-crystallized with a ligand, wherein the amino acid sequence of said beta secretase is SEQ ID NO:1, said crystal has trigonal space group symmetry P3$_2$21, a unit cell defined by the dimensions a, b, c, α, β, and γ wherein a=b=112 Å±20 Å, c=110 Å±20 Å, α=β=90 degrees, and γ=120 degrees, wherein said ligand is bound at the active site of said beta secretase, and has the following structure

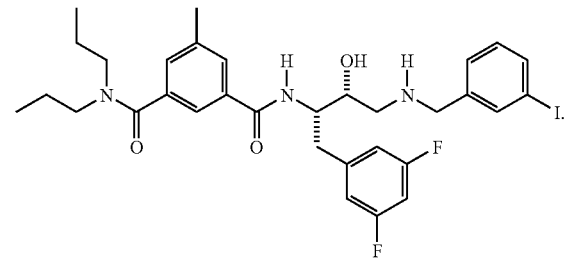

* * * * *

```
                        SEQUENCE LISTING

<160> NUMBER OF SEQ ID NOS: 5

<210> SEQ ID NO 1
<211> LENGTH: 385
<212> TYPE: PRT
<213> ORGANISM: Homo sapiens

<400> SEQUENCE: 1

Glu Met Val Asp Asn Leu Arg Gly Lys Ser Gly Gln Gly Tyr Tyr Val
1               5                   10                  15

Glu Met Thr Val Gly Ser Pro Pro Gln Thr Leu Asn Ile Leu Val Asp
                20                  25                  30

Thr Gly Ser Ser Asn Phe Ala Val Gly Ala Ala Pro His Pro Phe Leu
            35                  40                  45

His Arg Tyr Tyr Gln Arg Gln Leu Ser Ser Thr Tyr Arg Asp Leu Arg
        50                  55                  60

Lys Gly Val Tyr Val Pro Tyr Thr Gln Gly Lys Trp Glu Gly Glu Leu
65                  70                  75                  80

Gly Thr Asp Leu Val Ser Ile Pro His Gly Pro Asn Val Thr Val Arg
                85                  90                  95

Ala Asn Ile Ala Ala Ile Thr Glu Ser Asp Lys Phe Phe Ile Asn Gly
            100                 105                 110

Ser Asn Trp Glu Gly Ile Leu Gly Leu Ala Tyr Ala Glu Ile Ala Arg
        115                 120                 125

Pro Asp Asp Ser Leu Glu Pro Phe Phe Asp Ser Leu Val Lys Gln Thr
    130                 135                 140

His Val Pro Asn Leu Phe Ser Leu Gln Leu Cys Gly Ala Gly Phe Pro
145                 150                 155                 160

Leu Asn Gln Ser Glu Val Leu Ala Ser Val Gly Gly Ser Met Ile Ile
                165                 170                 175

Gly Gly Ile Asp His Ser Leu Tyr Thr Gly Ser Leu Trp Tyr Thr Pro
            180                 185                 190

Ile Arg Arg Glu Trp Tyr Tyr Glu Val Ile Ile Val Arg Val Glu Ile
        195                 200                 205

Asn Gly Gln Asp Leu Lys Met Asp Cys Lys Glu Tyr Asn Tyr Asp Lys
    210                 215                 220

Ser Ile Val Asp Ser Gly Thr Thr Asn Leu Arg Leu Pro Lys Lys Val
225                 230                 235                 240

Phe Glu Ala Ala Val Lys Ser Ile Lys Ala Ala Ser Ser Thr Glu Lys
                245                 250                 255

Phe Pro Asp Gly Phe Trp Leu Gly Glu Gln Leu Val Cys Trp Gln Ala
            260                 265                 270

Gly Thr Thr Pro Trp Asn Ile Phe Pro Val Ile Ser Leu Tyr Leu Met
        275                 280                 285

Gly Glu Val Thr Asn Gln Ser Phe Arg Ile Thr Ile Leu Pro Gln Gln
    290                 295                 300

Tyr Leu Arg Pro Val Glu Asp Val Ala Thr Ser Gln Asp Asp Cys Tyr
305                 310                 315                 320
```

```
Lys Phe Ala Ile Ser Gln Ser Ser Thr Gly Thr Val Met Gly Ala Val
                325                 330                 335

Ile Met Glu Gly Phe Tyr Val Val Phe Asp Arg Ala Arg Lys Arg Ile
            340                 345                 350

Gly Phe Ala Val Ser Ala Cys His Val His Asp Glu Phe Arg Thr Ala
        355                 360                 365

Ala Val Glu Gly Pro Phe Val Thr Leu Asp Met Glu Asp Cys Gly Tyr
    370                 375                 380

Asn
385

<210> SEQ ID NO 2
<211> LENGTH: 21
<212> TYPE: PRT
<213> ORGANISM: Artificial Sequence
<220> FEATURE:
<223> OTHER INFORMATION: Histidine Tag

<400> SEQUENCE: 2

Glu Gln Lys Leu Ile Ser Glu Glu Asp Leu Asn Met His Thr Glu His
1               5                   10                  15

His His His His His
            20

<210> SEQ ID NO 3
<211> LENGTH: 13
<212> TYPE: PRT
<213> ORGANISM: Artificial Sequence
<220> FEATURE:
<223> OTHER INFORMATION: Synthetic Peptide
<221> NAME/KEY: MOD_RES
<222> LOCATION: (5)..(5)
<223> OTHER INFORMATION: Statine

<400> SEQUENCE: 3

Ser Glu Val Asn Xaa Val Ala Glu Phe Arg Gly Gly Cys
1               5                   10

<210> SEQ ID NO 4
<211> LENGTH: 32
<212> TYPE: DNA
<213> ORGANISM: Artificial Sequence
<220> FEATURE:
<223> OTHER INFORMATION: Primer

<400> SEQUENCE: 4
cgctttggat ccgtggacaa cctgaggggc aa                                32

<210> SEQ ID NO 5
<211> LENGTH: 40
<212> TYPE: DNA
<213> ORGANISM: Artificial Sequence
<220> FEATURE:
<223> OTHER INFORMATION: Primer

<400> SEQUENCE: 5
cgctttggta ccctatgact catctgtctg tggaatgttg                        40
```